(12) United States Patent
Oldham et al.

(10) Patent No.: US 8,536,099 B2
(45) Date of Patent: Sep. 17, 2013

(54) METHODS OF BEAD MANIPULATION AND FORMING BEAD ARRAYS

(75) Inventors: Mark Oldham, Emerald Hills, CA (US); George Fry, San Carlos, CA (US); Christina Inman, San Mateo, CA (US); John Bridgham, Hillsborough, CA (US); Timothy Hunkapillar, Mercer Island, WA (US); Charles Vann, El Dorado Hills, CA (US)

(73) Assignee: Life Technologies Corporation, Carlsbad, CA (US)

( * ) Notice: Subject to any disclaimer, the term of this patent is extended or adjusted under 35 U.S.C. 154(b) by 217 days.

(21) Appl. No.: 12/872,333

(22) Filed: Aug. 31, 2010
(Under 37 CFR 1.47)

(65) Prior Publication Data
US 2011/0136677 A1 Jun. 9, 2011

Related U.S. Application Data

(60) Provisional application No. 61/238,633, filed on Aug. 31, 2009, provisional application No. 61/238,667, filed on Aug. 31, 2009, provisional application No. 61/307,623, filed on Feb. 24, 2010, provisional application No. 61/307,492, filed on Feb. 24, 2010, provisional application No. 61/307,641, filed on Feb. 24, 2010, provisional application No. 61/307,486, filed on Feb. 24, 2010.

(51) Int. Cl.
*C40B 30/00* (2006.01)
*C40B 30/04* (2006.01)
*C40B 30/08* (2006.01)
*C40B 30/10* (2006.01)

(52) U.S. Cl.
USPC .................. 506/7; 506/9; 506/11; 506/12

(58) Field of Classification Search
None
See application file for complete search history.

(56) References Cited

U.S. PATENT DOCUMENTS

| 3,736,042 A | 5/1973 | Markovitx et al. |
| 4,447,140 A | 5/1984 | Campbell et al. |

(Continued)

FOREIGN PATENT DOCUMENTS

| WO | 2008/002502 | 1/2008 |
| WO | 2011/026102 | 3/2011 |

(Continued)

OTHER PUBLICATIONS

Becker et al., Differential use of endoplasmic reticulum membrane for phagocytosis in J774 macrophages, Mar. 15, 2005, PNAS, vol. 102, No. 11, pp. 4022-4026.*

(Continued)

*Primary Examiner* — Ardin Marschel
*Assistant Examiner* — Karla Dines

(57) ABSTRACT

According to various embodiments, a method is provided that comprises washing an array of DNA-coated beads on a substrate, with a wash solution to remove stacked beads from the substrate. The wash solution can include inert solid beads in a carrier. The DNA-coated beads can have an average diameter and the solid beads in the wash solution can have an average diameter that is at least twice the diameter of the DNA-coated beads. The washing can form dislodged DNA-coated beads and a monolayer of DNA-coated beads. In some embodiments, first beads for forming an array are contacted with a poly(ethylene glycol) (PEG) solution comprising a PEG having a molecular weight of about 350 Da or less. In some embodiments, slides for forming bead arrays are provided as are systems for imaging the same.

20 Claims, 16 Drawing Sheets

(56) References Cited

U.S. PATENT DOCUMENTS

| | | |
|---|---|---|
| 4,705,705 A | 11/1987 | Bross |
| 5,143,854 A | 9/1992 | Pirrung et al. |
| 5,202,227 A | 4/1993 | Matsuda et al. |
| 5,324,591 A | 6/1994 | Georger, Jr. et al. |
| 5,510,270 A | 4/1996 | Fodor et al. |
| 5,776,748 A | 7/1998 | Singhvi et al. |
| 5,985,551 A | 11/1999 | Brennan |
| 6,548,263 B1 | 4/2003 | Kapur et al. |
| 6,921,636 B1 | 7/2005 | Brennan |
| 6,967,074 B2 | 11/2005 | Duffy et al. |
| 2003/0165935 A1 | 9/2003 | Vann et al. |
| 2004/0037739 A1 | 2/2004 | McNeely et al. |
| 2004/0219688 A1 | 11/2004 | Churchill et al. |
| 2005/0118589 A1 | 6/2005 | Vann et al. |
| 2006/0127939 A1 | 6/2006 | Woudenberg et al. |
| 2006/0286548 A1 | 12/2006 | Liposky et al. |
| 2009/0149341 A1* | 6/2009 | Walt et al. ............ 506/9 |
| 2011/0052446 A1 | 3/2011 | Hirano et al. |
| 2011/0124111 A1 | 5/2011 | Hoshizaki et al. |
| 2011/0128545 A1 | 6/2011 | Cox et al. |

FOREIGN PATENT DOCUMENTS

| | | |
|---|---|---|
| WO | 2011/026128 | 3/2011 |
| WO | 2011/026136 | 3/2011 |
| WO | 2011/026141 | 3/2011 |
| WO | 2011/026141 A3 | 3/2011 |
| WO | 2011/026128 A3 | 5/2011 |

OTHER PUBLICATIONS

Becker et al., PNAS, Mar. 15, 2005, vol. 102, No. 11, pp. 4022-4026.*
PCT/US2010/047392 International Search Report mailed Jan. 28, 2011.
LUDL Electronic Products LTD,"Filter Wheels-High Performance Filter Changers for Quantitative Microscopy", Retrieved from the Internet; URL:http://www.biovis.com/images/Automatio, n%20Page/Ludl/filterwheels.pdf>[retrieved on Nov. 8, 2011] the whole document, Online ; XP002608551; Bio Vision Technologies, Feb. 19, 2005.
PCT/US10/47308, Partial Search Report Mailed Nov. 11, 2010.
PCT/US10/47308, Written Opinion mailed Jan. 26, 2011.
PCT/US2010/047402, International Preliminary Report on Patentability mailed Mar. 6, 2012.
PCT/US2010/047402, Partial Search Report, Feb. 25, 2011.
PCT/US2010/047402, Written Opinion mailed Feb. 25, 2011.
PCT/US2010/47377, International Search Report and Written Opinion mailed Apr. 1, 2011.
PCT/US2010/47308, International Search Report and Written Opinion mailed Jan. 26, 2011.

* cited by examiner

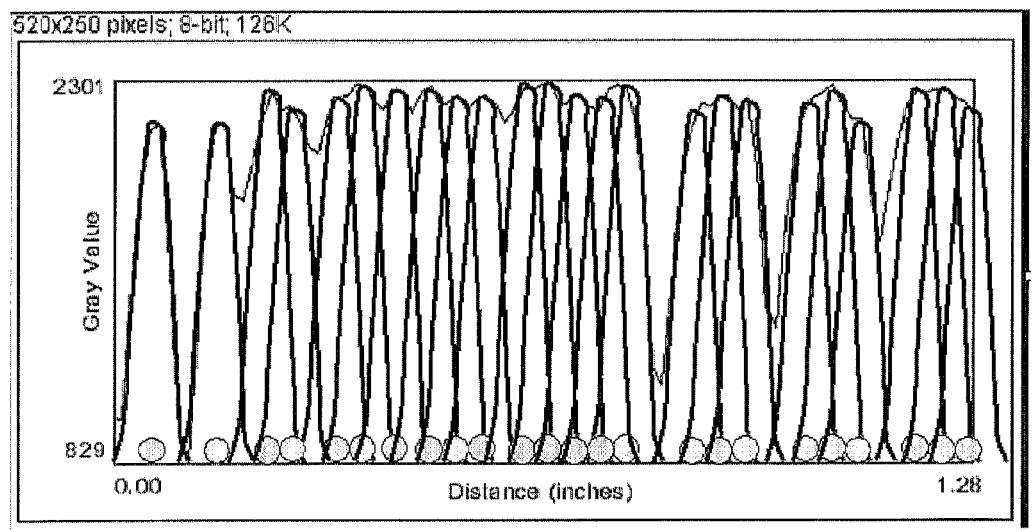
FIG. 10
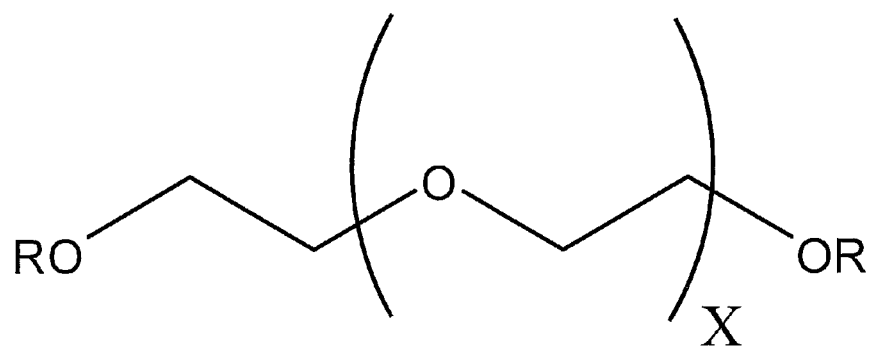
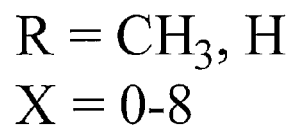
FIG. 11

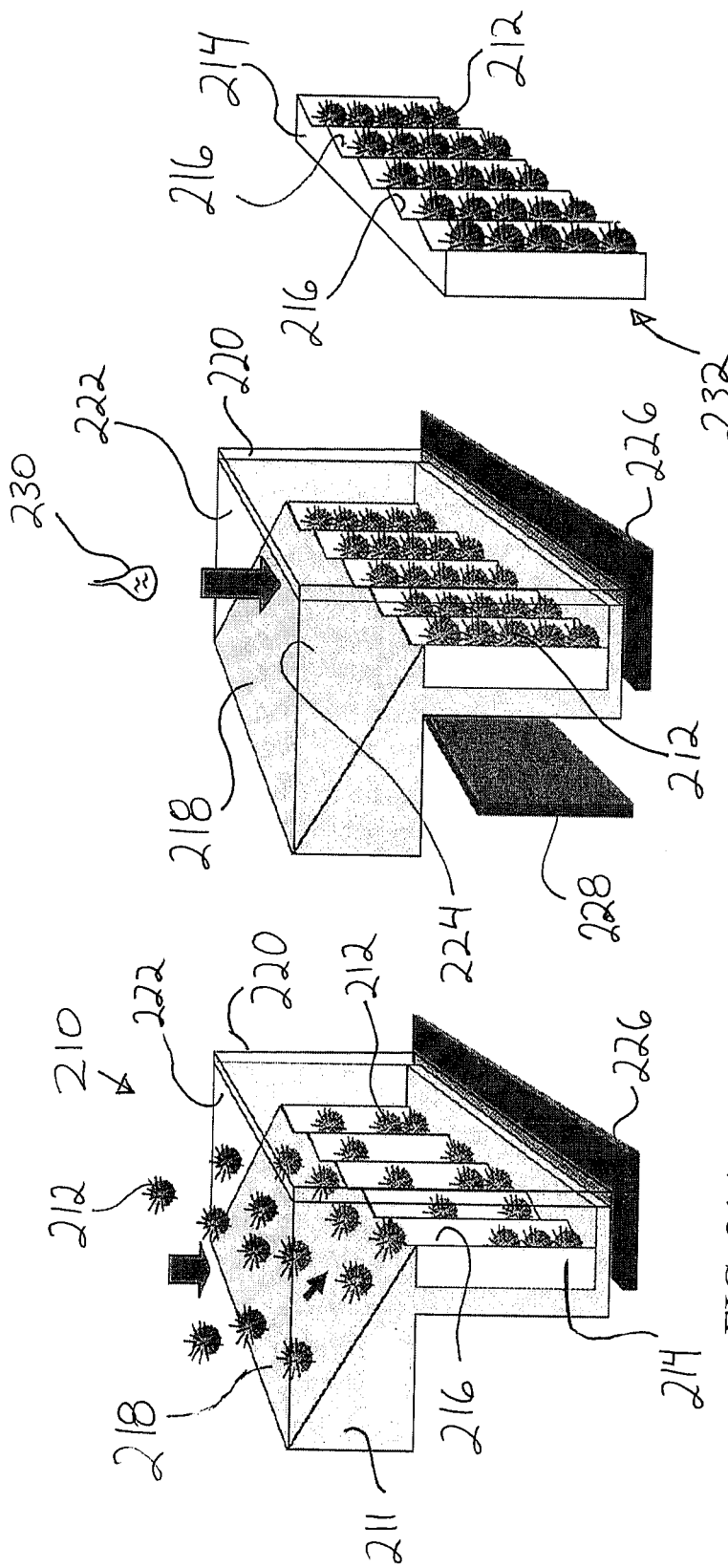

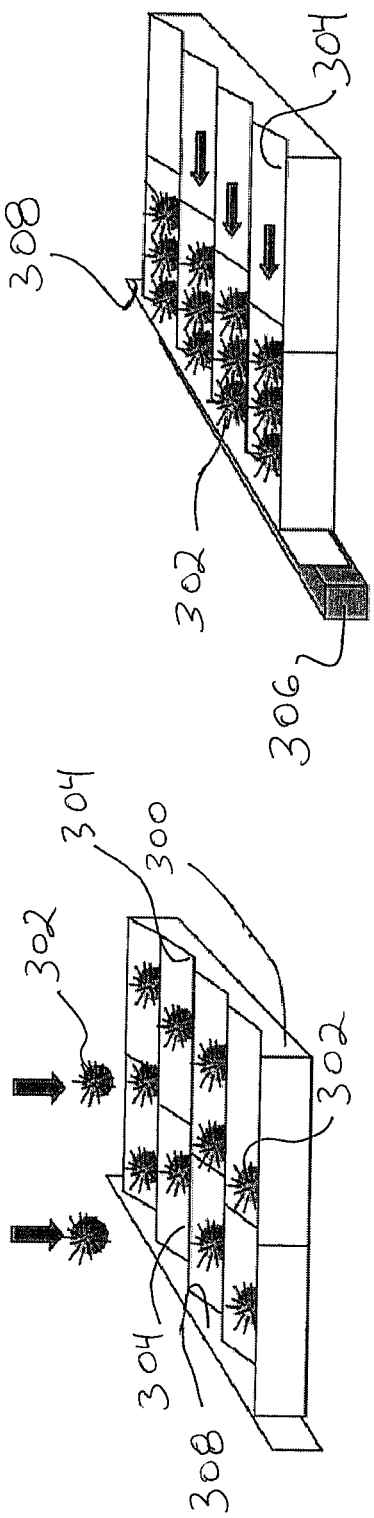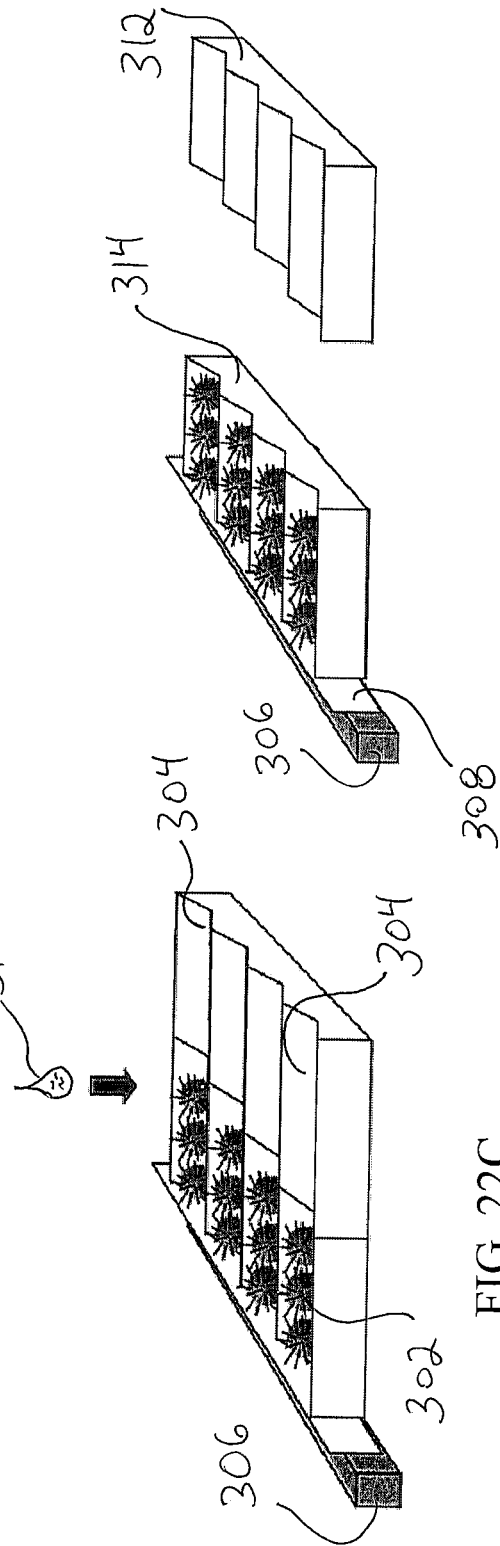
FIG. 22A
FIG. 22B
FIG. 22C
FIG. 22D

METHODS OF BEAD MANIPULATION AND FORMING BEAD ARRAYS

RELATED APPLICATIONS

This application claims priority pursuant to 35 U.S.C. §119 (e) to U.S. Provisional Patent Application Ser. No. 61/238,633, filed on Aug. 31, 2009, entitled "Enhanced Systems and Methods For Sequence Detection," U.S. Provisional Patent Application Ser. No. 61/238,667, filed on Aug. 31, 2009, entitled "Enhanced Flowcell and Reagent Delivery For Sequence Detection," U.S. Provisional Patent Application Ser. No. 61/307,623, filed on Feb. 24, 2010, entitled "Methods of Bead Manipulation and Forming Bead Arrays," U.S. Provisional Patent Application Ser. No. 61/307,492, filed on Feb. 24, 2010, entitled "Flowcells and Methods of Filling and Using Same," U.S. Provisional Patent Application Ser. No. 61/307,641, filed on Feb. 24, 2010, entitled "Flowcells and Methods of Filling and Using Same," and U.S. Provisional Patent Application Ser. No. 61/307,486, filed on Feb. 24, 2010, entitled "Flowcell, Flowcell Delivery System, Reagent Delivery System, and Method For Sequence Detection," the entirety of each of these applications being incorporated herein by reference thereto.

FIELD

The present disclosure is directed towards the field of molecular sequencing, in particular towards of solid-support/bead handling and forming ordered-arrays.

BACKGROUND

There is a challenge to pack beads modified with nucleic acid molecules, closely together to form an array for sequencing. It would be desirable to place nucleic acid-coated beads in an organized, tightly packed fashion, for example, to increase throughput per cycle and to lower customer cost per sequenced base. As the bead deposition density is increased, however, the likelihood of bead clumping and bead stacking increases. Controlled organization of the bead would also simplify software identification of the beads on the surface. Unfortunately, when the beads are stacked or clumped, there can be problems with interrogation for their individual reporter signals.

In sequencing using beads, the overall throughput in terms of nucleic acid bases sequenced per sequencing run is directly dependent on the number of readable beads in a given interrogation area, and generally, the more the better. When beads are dispensed randomly onto a slide, a considerable amount of space on the slide is left open. Furthermore, some beads settle on the slide overlapping and/or stacking with several other beads, which can cause difficulties in resolving and interpreting images of the beads.

When imaging an array of beads, for example, fluorescently labeled beads for nucleic acid sequencing, it is desirable to have the beads packed as densely as possible to achieve the highest throughput. However, issues may arise for beads of a size such that the diffraction circles or spread function is relatively large compared to the actual bead size. For example, a one micron diameter bead could have a diffraction circle of about 2 microns. Packing the beads at a density such that the beads are all or mostly all touching each other results in un-resolvable features, whether these beads are randomly arrayed or ordered in a close pack.

SUMMARY

According to various embodiments, a method is provided that includes washing an array of first beads on a substrate with a wash solution to remove stacked beads from the substrate. The wash solution can comprise from about 2% by weight to about 50% by weight inert solid beads in a carrier. The solid beads in the wash solution can have an average diameter that is larger than the first beads, for example, at least twice the diameter of the first beads. The washing can form dislodged first beads. The method can comprise removing the wash solution and the dislodged first beads from the substrate to form a monolayer of first beads. In some embodiments, the substrate can comprise a slide. In some embodiments, the substrate can comprise a plurality of channels formed in a surface thereof. The first beads can comprise DNA-coated beads. In some embodiments, the wash solution can comprise first abrasive beads having a second average diameter, and second abrasive beads having a third average diameter, and the second average diameter can be about 50% greater than the third average diameter.

According to various embodiments, a method of forming an ordered array of beads is provided that comprises contacting a plurality of first beads with a poly(ethylene glycol) ("PEG") solution comprising a PEG having an average molecular weight of about 350 Da or less, to form a bead mixture, and depositing the bead mixture on a surface of an array substrate. In some embodiments, the PEG can have a molecular weight of about 200 Da. The array substrate can comprise a slide having a plurality of grooves formed in a surface thereof, and the bead mixture can be deposited into the grooves.

According to various embodiments, an ordered array of beads is provided that comprises a substrate comprising hydrophobic lines in the shape of a grid and at least one hydrophilic area defined between the hydrophobic lines. A monolayer of assay beads can be provided at each of the at least one hydrophilic areas. In some embodiments, the ordered array of beads comprises hydrophobic lines, a hydrophilic area, a combination thereof, or multiples thereof, or a coated or uncoated surface, that comprises a pattern of photoresist, polydimethylsiloxane, metal, glass, metal oxide, or plastic.

Various embodiments of a method is provided which includes washing an array of first beads on a substrate, with a wash solution to remove stacked beads from the substrate, the wash solution comprising from 2% to 50% by weight inert solid beads in a carrier, the first beads having an average diameter and the solid beads having an average diameter that is at least twice the diameter of the first beads, the washing forming dislodged first beads. In some embodiments, the methods include removing the wash solution and the dislodged first beads from the substrate to form a monolayer of first beads. In some embodiments, the substrate can include a slide, and the substrate can also include a plurality of channels formed in a surface thereof.

In some embodiments, the first beads can include DNA-coated beads. In some embodiments, the carrier can include water. In some embodiments, the wash solution can include first abrasive beads having a second average diameter, and second abrasive beads having a third average diameter, and the second average diameter is at least 50% greater than the third average diameter.

Various embodiments of a method of forming an ordered array of beads are also disclosed herein. In some embodiments, the method includes contacting a plurality of first beads with a poly(ethylene glycol) (PEG) solution comprising a PEG having a molecular weight of about 350 Da or less, to form a bead mixture, and depositing the bead mixture on a surface of an array substrate. The PEG can include various molecular weights, for example, about 200 Da. In some embodiments, the array substrate can include a slide having a plurality of grooves in a surface thereof, and the depositing comprises depositing the bead mixture into the grooves.

Various embodiments of an ordered array of beads are also provided herein. In some embodiments, the array of beads includes a substrate comprising hydrophobic lines in the shape of a grid and at least one hydrophilic areas defined between the hydrophobic lines. The array can also include a monolayer of assay beads each of the at least one hydrophilic areas. In some embodiments, the ordered array of beads can include at least one of the hydrophobic lines and the at least one hydrophilic area comprise a pattern of photo-resist, polydimethylsiloxane, metal, glass, metal oxide, or plastic.

Various embodiments of a method of imaging a plurality of uniformly-sized beads in a bead array are also provided herein. In some embodiments, the methods include arranging a plurality of uniformly-sized beads in a plurality of grooves in a grooved substrate to form an array, the grooves being spaced apart by a pitch equal to about 110% or more of a diameter of the beads, the beads forming a plurality of single-file rows of beads in the respective grooves, wherein adjacent beads in each respective row are touching one another, each bead comprises a respective analyte fixed to a surface thereof, and the respective analyte of each bead is different than the respective analyte of at least one other bead of the plurality. The method can also include exciting the plurality of beads in the array such that a portion of the beads become excited, emitting an increased radiation intensity relative to a portion of the other beads, and imaging the area with an optics system configured to resolve adjacent grooves of the plurality of grooves but not to resolve adjacent excited beads within a same groove, the imaging forming an image array data set. The method can also include identifying the position of each bead in the array and whether or not it is excited based on the array data set, wherein the positions of unresolvable adjacent excited beads within a same groove are determined from identifying unresolved groups of quantized length.

In some embodiments, the portion of the plurality of beads comprises about 30% or less of the total number of beads. In some embodiments, the exciting comprises exposing the array to at least four different excitation conditions, and the imaging comprises generating a plurality of array data sets, each array data set representing the array under a different excitation condition. The method can further include further comprising determining a sequence of each different analyte based on the plurality of array data sets. In some embodiments, the pitch can be from about 125% to about 300% of the diameter, about 140% to about 160% of the diameter, etc.

Various embodiments of a system are also provided herein. In some embodiments, the system includes a substrate comprising a plurality of grooves formed in a surface thereof, the grooves being spaced apart from one another at a pitch, and a plurality of beads disposed in the grooves and forming an array, wherein for each groove a plurality of the beads forms a row of beads in the groove and adjacent beads in the row touch one another, the beads having a diameter, and the pitch being from about 125% to about 300% of the diameter. In some embodiments, the system can include an imaging system having a resolution sufficient to resolve adjacent rows but insufficient to resolve adjacent beads within a same row under excited conditions, the excited conditions comprising conditions whereby increased radiation is emitted from the bead compared to radiation emitted from the same bead under non-excited conditions, the imaging system being configured to generate an array data set. The system can also include a processor configured to identify the position of each bead in the array based on the array data set, wherein the positions of unresolvable adjacent excited beads within a same groove are determined from identifying unresolved groups of quantized length. In some embodiments, the system of claim 18, the pitch can be, for example, from about 140% to about 160% of the diameter. In some embodiments, the system can further include an excitation source configured to direct an excitation beam toward the array under at least one set of excitation conditions. In some embodiments, the at least one set of excitation conditions comprises at least four different sets of excitation conditions.

Various embodiments of a device are also provided herein. In some embodiments, the device includes a substrate, and a plurality of posts extending from a surface of the substrate, wherein the plurality of posts comprise a plurality of post clusters. In some embodiments, one or more of the post clusters define bead receiving areas between posts, each bead receiving area is configured to retain a single bead of a predetermined bead diameter of about 10 µm or less, each post comprises a base portion and a tip, and the cross-sectional area of the post decreases in a direction from the base portion to the tip.

In some embodiments, the post clusters are arranged to provide a center-to-center spacing of adjacent beads when disposed in the device, of from about 1.1 to about 1.9 times the diameter of a bead of the predetermined diameter. In some embodiments, the post clusters are arranged to provide a center-to-center spacing of adjacent beads when disposed in the device, of from about 1.2 to about 1.6 times the diameter of a bead of the predetermined diameter. In some embodiments, the post clusters are arranged to provide a center-to-center spacing of adjacent beads, when disposed in the device, of about 1.5 times the diameter of a bead of the predetermined diameter. In some embodiments, the substrate comprises an injection-molded cyclo-olefin polymer material. In some embodiments, the device further includes a plurality of beads including one bead at each bead receiving area.

In some embodiments, the device further includes at least one fiducial post disposed in at least one of the bead receiving areas, the at least one fiducial post configured to prevent a bead from being received in the respective bead receiving area. The fiducial post can extend further from the surface than each post of the plurality of posts. In some embodiments, the device can further include a plurality of beads disposed in the bead receiving areas and forming an array, wherein the center-to-center spacing of the beads in the array is from about 115% to about 190% of the diameter of the beads.

Various embodiments of a system comprising some embodiment of the presently disclosed device is also provided herein. In some embodiments, the system further includes an imaging system having a resolution sufficient to resolve adjacent rows but insufficient to resolve adjacent beads within a same row under excited conditions, the excited conditions comprising conditions whereby increased radiation is emitted from the bead compared to radiation emitted from the same bead under non-excited conditions, and the imaging system being configured to generate an array data set. In some embodiments, the system further comprises a processor configured to identify the position of each bead in the array based on the array data set.

Various embodiments of a method of loading a plurality of magnetic beads into grooves of a grooved plate are also provided herein. In some embodiments, the method includes arranging a plate comprising grooves on a support such that grooves are vertically arranged, the support comprising an inclined surface and the grooves comprising respective first ends arranged adjacent the inclined surface, and respective open tops, and disposing a plurality of beads on the inclined surface such that the beads traverse the inclined surface and enter the grooves at the first ends. In some embodiments, the method can also include guiding the beads into the grooves in a manner such that beads in each groove are aligned with one another in the respective groove, the guiding comprising placing a guide wall adjacent the open tops in sufficiently close proximity to prevent the beads in any one of the grooves from moving into another one of the grooves, and fixing the beads in the grooves.

In some embodiments, the method further includes separating the guide wall from adjacent the open tops and separating the plate from the support. In some embodiments, the plate comprises a first portion and a second portion, and the method comprises separating the first portion from the second portion after fixing the beads in the grooves and separating the plate from the support.

In some embodiments, the fixing the beads in the grooves step can include comprises contacting the beads with a chemical fixing agent. In some embodiments, fixing the beads in the grooves can include magnetically attracting the beads against surfaces of the grooves or photoactively attaching the beads to the surfaces of the grooves. In some embodiments, guiding the beads into the grooves can include magnetically attracting the beads into the grooves.

Various embodiments of a method of loading a plurality of magnetic beads into grooves of a grooved plate are also provided herein. In some embodiments, the method includes providing a plate. In some embodiments, the plate can include a load portion, an excess portion, a plurality of grooves each having a respective open first end on the excess portion, a respective closed second end on the load portion, and a respective open top, the second ends being closed by a sidewall, the sidewall comprising an interior surface facing the respective groove and an exterior surface facing away from the groove. The method can also include positioning a magnet adjacent the exterior surface of the sidewall, loading magnetic beads into the open ends of the grooves, magnetically attracting the magnetic beads into the grooves, using the magnet, such that the beads in each groove align with one another, and separating the load portion from the excess portion. The method can also include fixing the beads in the grooves.

These and other embodiments of the present disclosure are detailed below.

BRIEF DESCRIPTION OF THE DRAWINGS

The present disclosure will be more fully understood from the following detailed description taken in conjunction with the accompanying drawings, in which:

FIG. 10 shows the spacing of an ordered array deposition without using a PEG additive;

FIG. 11 shows the chemical structure of an exemplary PEG additive that can be used according to various embodiments of the present teachings;

FIGS. 21A-21C depict three successive steps of a method and configuration for magnetically loading and fixing beads into grooves of a slide, according to various embodiments of the present teachings; and FIGS. 22A-22D depict four successive steps of a method and configuration for magnetically loading and fixing beads into grooves of a slide, and removing an excess slide portion, according to various embodiments of the present teachings.

DETAILED DESCRIPTION

Figure 1A:
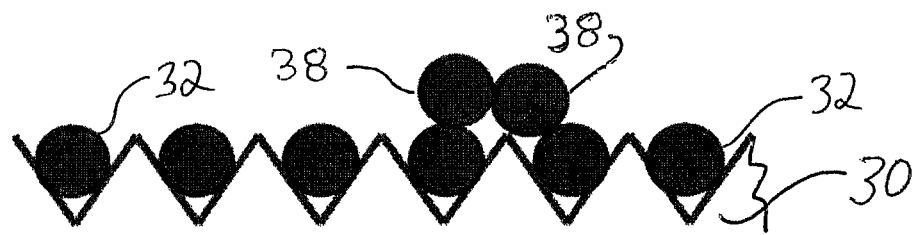
FIGS. 1A-1D provide an overview of a microabrasive solution treatment method according to various embodiments of the present teachings.

According to various embodiments, a method is provided that comprises washing an array of first solid-supports (e.g., beads) on a substrate, with a wash solution to remove stacked beads from the substrate. The wash solution can comprise from about 2% by weight to about 50% by weight inert solid beads in a carrier, for example, from about 5% by weight to about 20% by weight, or from about 9% by weight to about 10% by weight. The first beads have an average diameter and the solid beads in the wash solution have an average diameter that is larger than the average diameter of the first beads, for example, at least twice the diameter of the first beads. The washing can form dislodged first beads. The method can comprise removing the wash solution and the dislodged first beads from the substrate to form a monolayer of first beads. In some embodiments, multiple washes are used. In some embodiments, the substrate can comprise a slide. In some embodiments, the substrate can comprise a plurality of channels formed in a surface thereof. In some embodiments, the first beads can comprise polynucleotide-coated beads or beads coated (or at least partially coated with some other biomolecule). In some embodiments, the carrier can comprise water, alcohol, or another carrier that does not interact with polynucleotide-coated first beads. In some embodiments, the wash solution can comprise first abrasive beads having a second average diameter, and second abrasive beads having a third average diameter, and the second average diameter can be at least 25% greater, at least 50% greater, or at least 75% greater than the third average diameter.

According to various embodiments, the micro-abrasive bead wash solution and method using the same removes stacked beads on ordered array slides, increasing usable beads for sequencing. The ability to remove stacked beads increases the ability to deposit more beads per ordered array slide, which can increase throughput of a sequencing instrument. The ability to remove stacked beads results in a monolayer of beads on the surface and aids in image focusing. Removing stacked beads enables the detection of beads underneath a stack, whereas if there is a stack of two or more beads neither can be successfully interrogated. The ability to remove stacked beads also reduces signal noise, which reduces errors. The ability to remove stacked beads also improves the functionality of automated imaging systems to detect beads. Moreover, the ability to remove stacked beads enables an increase in the number of beads per ordered array slide, reducing the cost per sequenced base on a sequencing instrument.

According to various embodiments, beads can be dispersed on a substrate to form a bead array. Initially, the beads can be dispersed in a random fashion on a substrate, for example, on a glass slide. The initial deposition can result in variation in bead density and, sometimes, clumping of beads. According to the present teachings, ordered array substrates are provided to organize beads on the surface of a substrate for sequencing. To minimize bead stacking in high density arrays, a method is provided to remove the stacked beads, reduce the production of stacked beads, and reduce bead to bead interaction.

In some embodiments, a micro-abrasive bead wash solution and wash method is provided to remove stacked beads from a slide following initial bead deposition on the slide. After depositing a high density of beads, for example, greater than about 200,000 beads per panel concentration, the deposition chamber liquid can be exchanged with a micron bead solution. In some embodiments, the micron bead solution can act as an abrasive and remove most stacked beads on the slide, leaving a single layer of beads. By removing stacked beads, this micro-abrasive bead wash solution and the method of using the solution enable increased density loading of beads. The result is increased instrument throughput as the array of beads thus formed on the surface can then be individually interrogated, for example, individually identified and sequenced.

According to various embodiments, a solution of beads is used as an abrasive to remove stacked beads on an ordered array slide. In some embodiments, following deposition of polynucleotide-coated beads onto an ordered array slide substrate, a micro-abrasive bead solution can be pipette onto the slide, for example, inside a chamber covering the polynucleotide-coated bead array. The solution can be caused to flow over the deposited beads. The beads in the micro-abrasive solution can be made to bump into stacked beads on the slide, and disrupt their attachment to other beads on the surface. This action removes the stacked beads, resulting in a monolayer of beads on the array slide surface. The monolayer of beads can be interrogated, the beads can be individually resolved, and the array can be useful for a ligation assay, a hybridization assay, or the like. The ability to clear away stacked beads on an ordered array slide allows for increased deposition of beads beyond the saturation point that would otherwise be limiting due to stacked beads.

In some embodiments, the micro-abrasive bead can be monodispersed, that is, of uniform-sized beads with little to no deviation in size. In some embodiments, the solution can comprise a mixture of two different sized beads, for example, comprising beads of about 3 micron average diameter and beads of about 5 micron average bead diameter. Larger beads can be used to facilitate movement of smaller beads, and in the example just described, the 5 micron average diameter beads can facilitate movement of the 3 micron average diameter beads when they bang into each other. Depending on the size of the polynucleotide-coated beads forming the monolayer array, the larger sized beads can be used to disrupt larger groups of stacked beads.

The abrasive solution beads can comprise silica, silicon nitride, boron nitride, other inert, hard materials, or the like. The density of the abrasive solution beads can be from about 1.0 grams per cubic centimeter (g/cc) to about 3.0 g/cc, for example, from about 1.5 g/cc to about 2.5 g/cc, or about 2.0 g/cc. In some embodiments, silica beads of a density of about 2.0 g/cc are used.

Figure 1B:
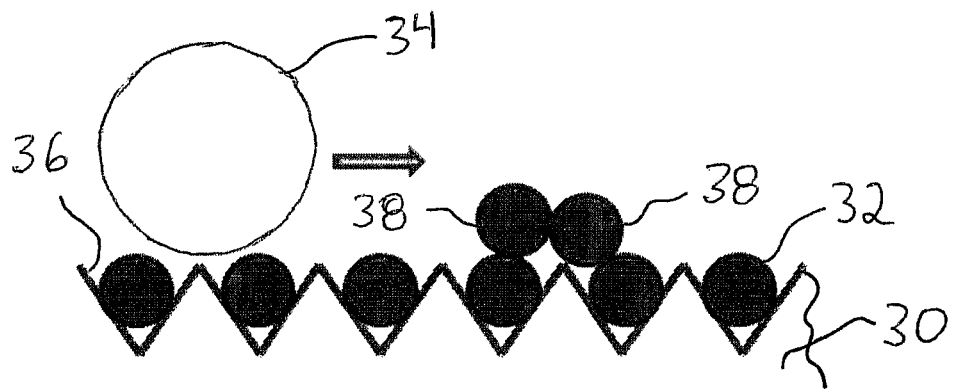
Figure 1C:
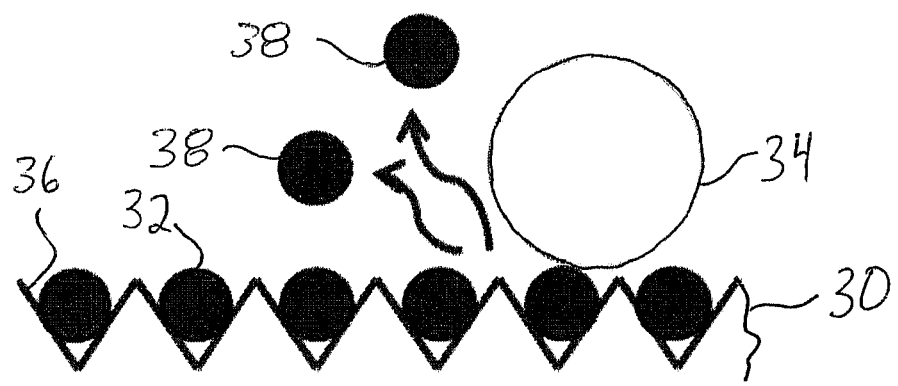
Figure 1D:
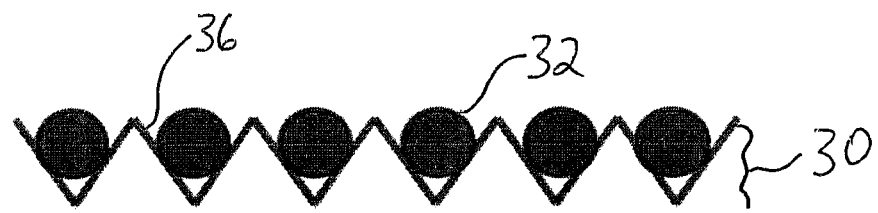

FIGS. 1A-1D show an overview of a microabrasive method according to various embodiments of the present teachings. In FIG. 1A, an ordered array slide 30 having a plurality of DNA-coated beads 32 is shown as DNA-coated beads 32 are initially deposited. In FIG. 1B, a solution containing 3-5 micron abrasive beads 34 is poured over DNA-coated beads 32 on the grooved surface 36 of slide 30. Slide 30, covered with micro-abrasive solution and beads 34, is then is placed on a Roto-Torque and rocked so that beads 34 in the micro-abrasive solution bombard stacked beads 38 and dislodge stacked beads 38 from surface 36, as shown in FIG. 1C. As can be seen in FIG. 1D, after treatment, the microabrasive solution and dislodged beads are removed from surface 36 and slide 30 is ready for sequencing.

Figure 2:
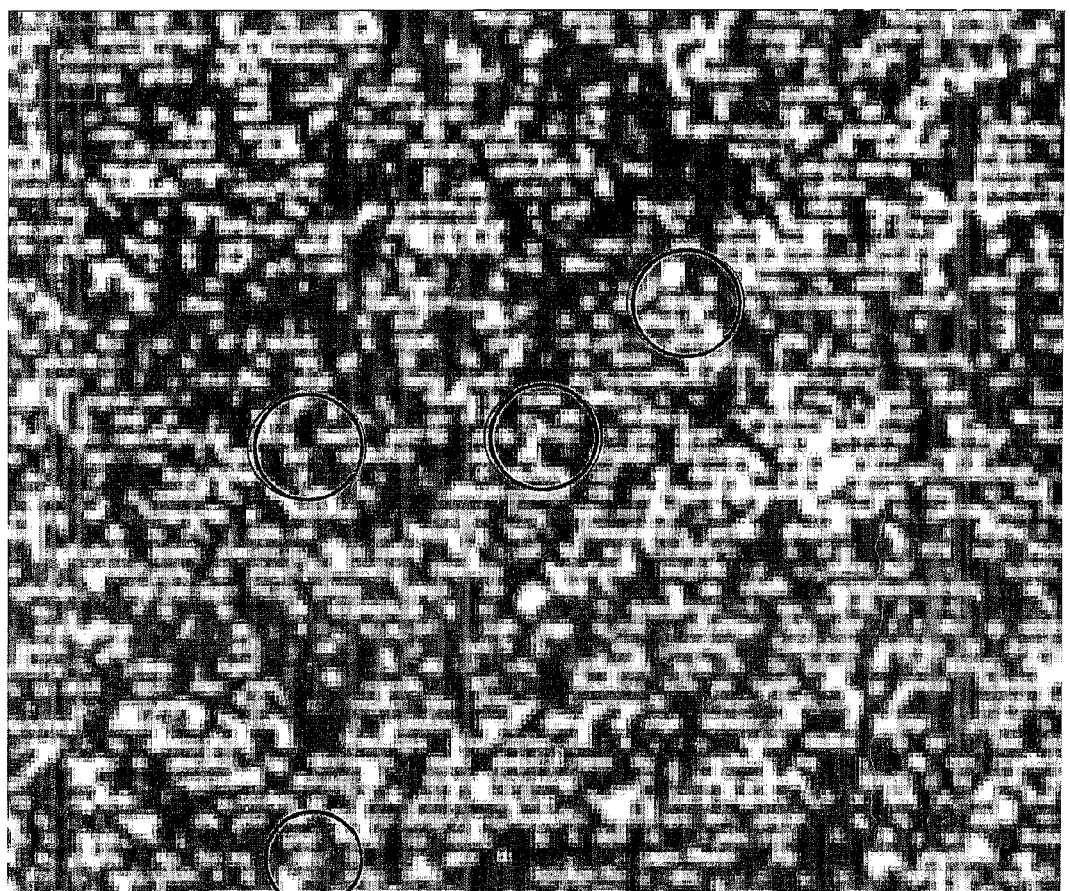
FIG. 2 is a white light image of a bead array that includes clumped stacks of bead, taken from an Olympus microscope at 20× magnification and then digitally enhanced to 400%.

FIG. 2 is a white light image taken from an Olympus microscope at 20× magnification and then digitally enhanced to 400%. The image is from an ordered array slide after deposition of beads at a concentration of 240,000 1024-synthetic beads per panel area. The image shows individual beads, and clumped stacks 40 of beads. The circles mark a few examples of clumped stacks 40 covering an underlying mono-layer of beads.

Figure 3:
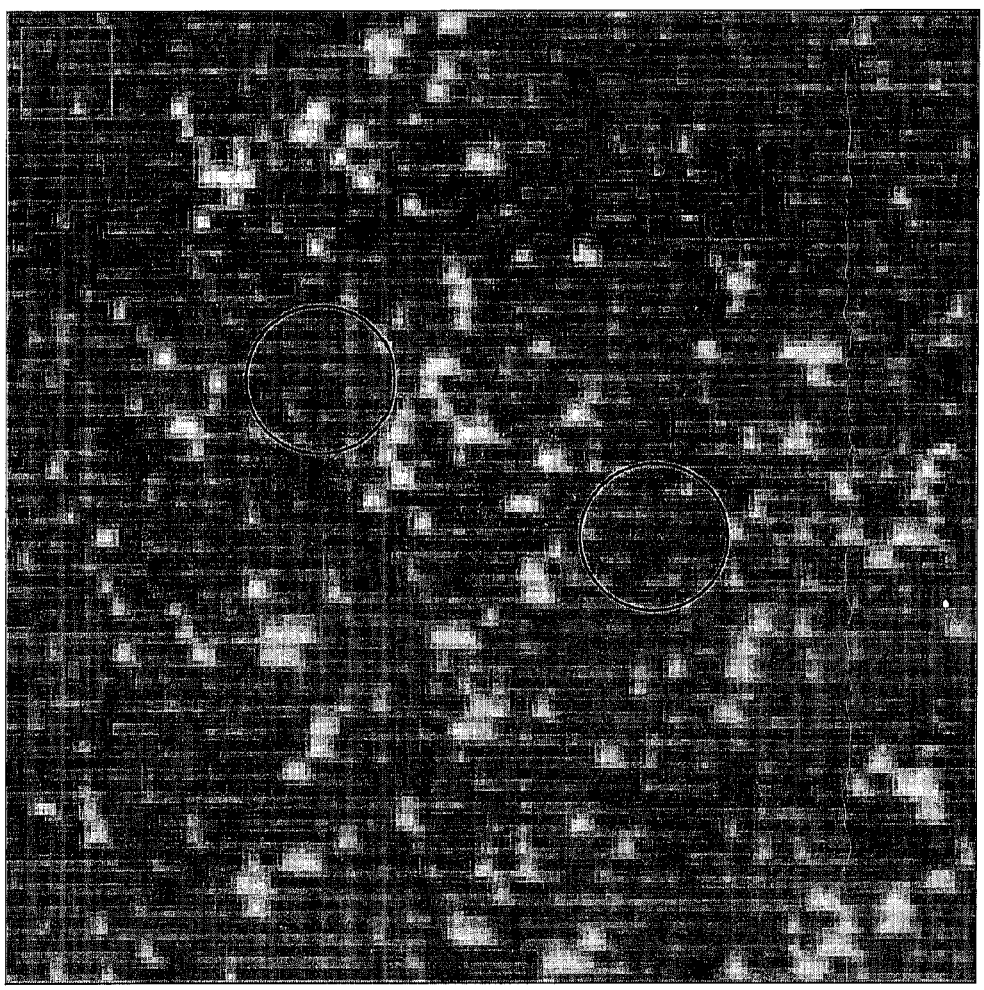
FIG. 3 is a white light image of the same bead array substrate shown in FIG. 2 following a wash treatment according to various embodiments of the present teachings and enhanced to 600%.

FIG. 3 is a white light image of a bead array taken with an Olympus microscope at 20× magnification. The image has been digitally enhanced to a 600% image. The image is of the same as that taken of FIG. 2 but after the ordered array slide has been subject to a bead abrasive wash treatment according to the present invention. As can be seen, the image shows that the wash greatly reduced the population of stacked beads in the array, and increased the mono-layer area of the array as particularly shown in the circled portions.

According to yet other various embodiments of the present teachings, to increase the mappable bead loading on a slide, an ordered array slide is provided that can align deposited beads into slots or grooves. By aligning the beads on the surface, better bead-finding algorithms can be designed to detect and analyze the beads. In some embodiments, beads are deposited on, for example, a metal-treated glass slide by settling on the surface. Sometimes, however, random bead attachment all over the slide results, not just in the slots or grooves. Addition of the beads to the deposition chamber, followed by immediate centrifugation, can result in the beads depositing into the slot/grooves. In some embodiments, to increase bead binding within slots or grooves, a method is provided to slow down bead attachment to the slide surface, which allows the beads time to move into the slots or grooves before attachment to the surface. The method can utilize a novel additive to the deposition solution to deposit the beads into the slots or grooves, without hindering the attachment chemistry.

According to various embodiments, a method of forming an ordered array of beads is provided that comprises contacting a plurality of first beads with a PEG solution comprising a PEG having an average molecular weight of about 350 Da or less, to form a bead mixture, and depositing the bead mixture on a surface of an array substrate. In some embodiments, the PEG can have an average molecular weight of about 200 Da. The array substrate can comprise a slide having a plurality of grooves formed in a surface thereof, and the bead mixture can be deposited into the grooves.

In some embodiments, PEG is added to the bead deposition solution acts to slow down the attachment process and reduce bead-to-bead clumping and sticking, while still maintaining the bead attachment chemistry. This enables the use of an ordered array for SOLiD sequencing. The distribution of beads during bead deposition to form an ordered array can be dependent on the molecular weight of the PEG additive used in the deposition solution. In some embodiments, the PEG used has a molecular weight range that aids bead deposition into the slots or grooves of the slide. In some embodiments, the PEG used has an average molecular weight of from about 100 Daltons (Da) to about 300 Da, for example, from about 150 Da to about 250 Da, or about 200 Da. In some embodiments, not only does the PEG additive aid in depositing the beads into the slide grooves, but also results in a small, reproducible spacing between the beads on the surface. This reduces the bead-to-bead contact. The result is an increase in the ability of the bead mapping software to identify and interpret bead reporter signals during sequencing.

Figure 4:
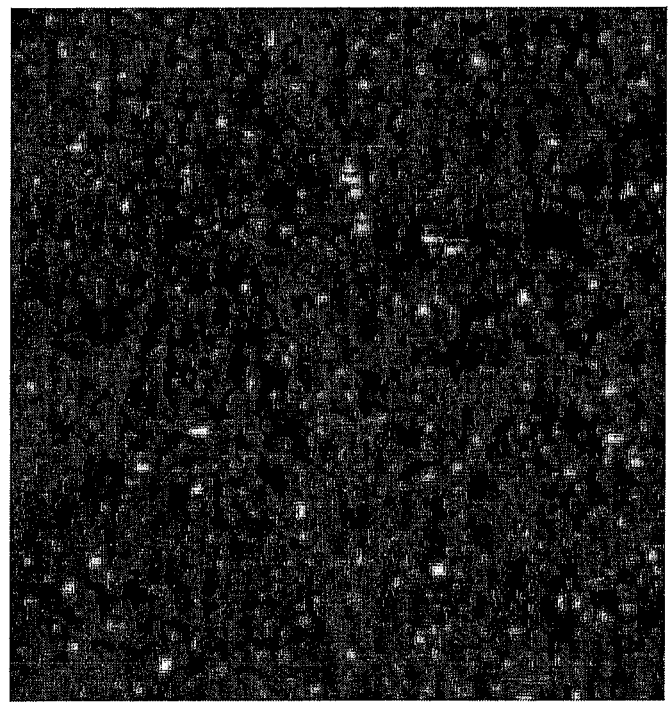
FIG. 4 shows a deposition method by settling, without centrifugation in 12% PEG 100 mM NaCl solution.

FIG. 4 shows a deposition method by settling, without centrifugation in 12% PEG 100 mM NaCl solution. The image shows high degree of bead stacking and clumping randomly all over the ordered array slide and not deposited into the slots/grooves. The image is a white light image from an Olympus microscope at 20× magnification digitally enhanced to a 400% image.

Figure 5:
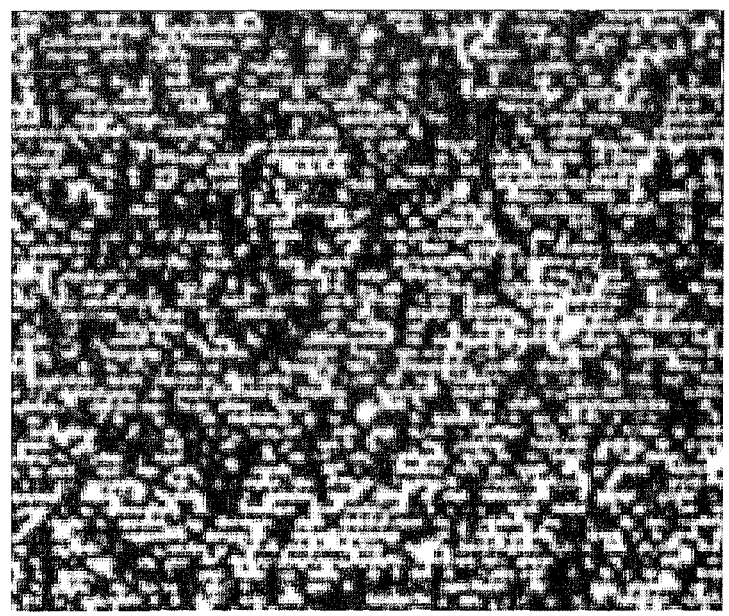
FIG. 5 shows bead deposition where the beads were deposited using a solution of 100 mM NaCl without a PEG additive.

FIG. 5 shows bead deposition after treatment with a solution of 100 mM NaCl without a PEG additive. In the array shown in FIG. 5, sonicated beads were delivered to a deposition chamber, the chamber was sealed, and then centrifuged within 2-minutes. The image shows improved deposition into the grooves but also a high degree of bead stacking and clumping on the slide surface. The image is a white light image from an Olympus microscope at 20× magnification digitally enhanced to a 400% image.

Figure 6:
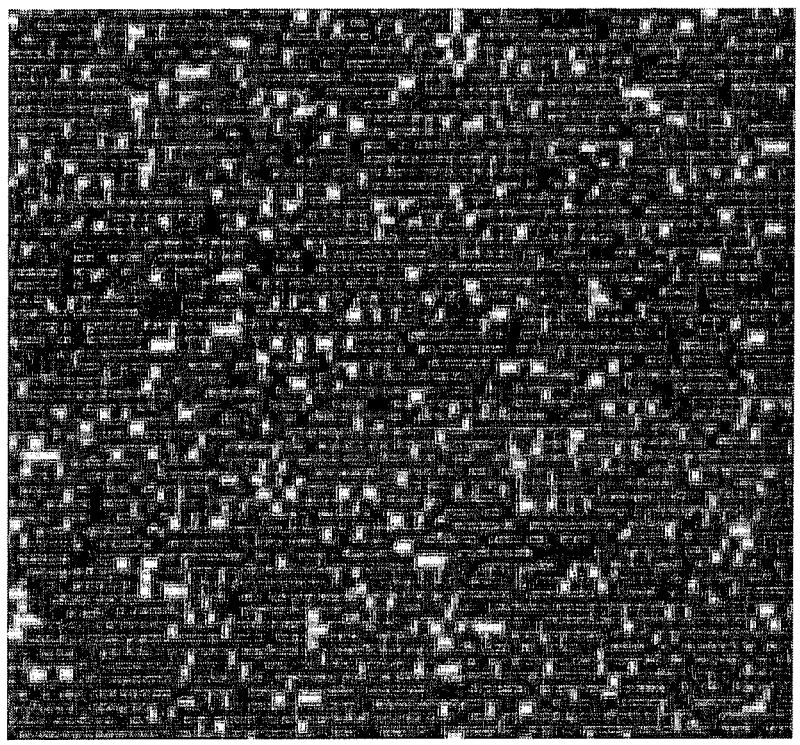
FIG. 6 shows about 280,000 beads per panel deposited onto an ordered array slide using as an additive a 200 Da MW PEG in 100 mM of NaCl.

FIG. 6 shows 280,000 beads per panel deposited onto an ordered array slide using as an additive a 200 Da MW PEG in 100 mM of NaCl. The image is a white light image from an Olympus microscope at 20× magnification digitally enhanced to a 400% image.

Figure 7:
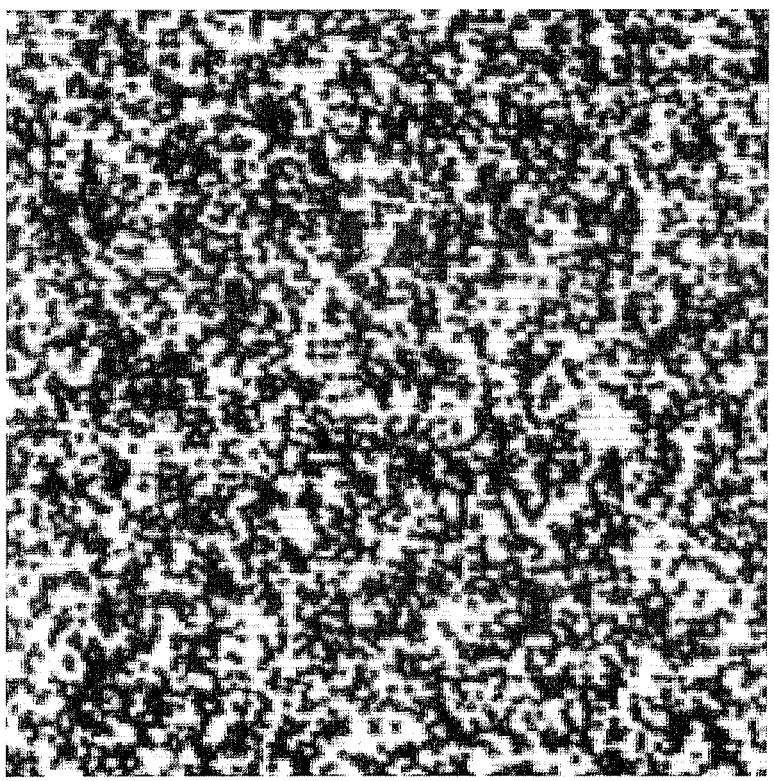
FIG. 7 shows about 280,000 beads per panel deposited onto an ordered array slide using as an additive a 350 Da MW PEG in 100 mM NaCl.

FIG. 7 shows 280,000 beads per panel deposited onto an ordered array slide using as an additive a 350 Da MW PEG in 100 mM NaCl. The image is a white light image from an Olympus microscope at 20× magnification digitally enhanced to a 400% image.

Figure 8:
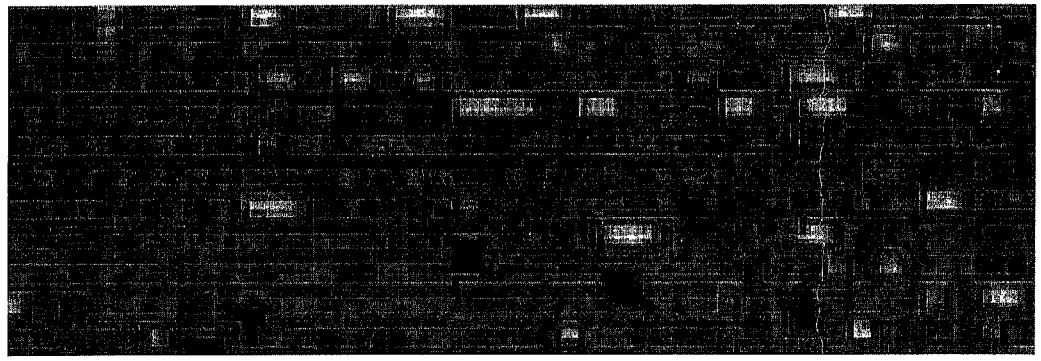
FIG. 8 shows a zoomed into image by way of pixel enhancement of the 20× optical image shown in FIG. 7 and showing 1-micron diameter individual beads deposited into the grooves on an ordered array slide.

FIG. 8 shows a zoomed into image by way of pixel enhancement of the 20× optical image shown in FIG. 7 and showing 1-micron diameter individual beads deposited into the grooves on an ordered array slide. As can be seen, individual beads are clearly identifiable.

Figure 9:
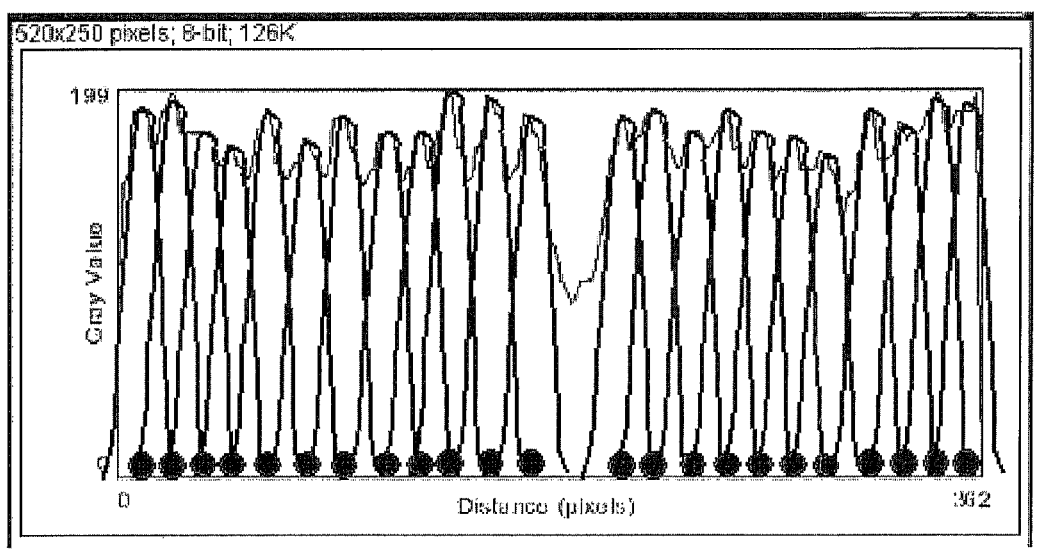
FIG. 9 shows the spacing of an ordered array deposition using a PEG additive.

FIG. 9 shows the spacing of an ordered array deposition using a PEG additive. The image represents beads to scale and single bead spread function to determine distance. There is an almost regular gap between beads with 23 beads shown in a 33.5 μm region showing an average spacing distance of from about 0.1 to 0.15 microns.

FIG. 10 shows the spacing of an ordered array deposition without using a PEG additive. The image scanned represents beads to scale and used single bead spread function to determine distance. As is shown, 24 beads are distributed in the 33.5 μm region scanned. Essentially the same bead deposition level as the regularly spaced beads results although in this case beads are clustered in groups of touching beads.

FIG. 11 shows the chemical structure of an exemplary PEG additive that can be used according to various embodiments of the present teachings, for example, that can be used in making an ordered bead array for a SOLiD system.

In some embodiments, the bead spacing or gap can be regular enough to be measured when compared to a non-PEG deposited ordered array slide. FIGS. 5 and 6 show a comparison between an ordered array slide made according to the present teachings (FIG. 6) and an ordered array slide made without using PEG (FIG. 5). As can be seen, the PEG additive increases the interrogation ability of high density arrays and increases bead loading as well as keeps the beads isolated on the slide.

In some embodiments, a PEG molecule is added to the bead deposition solution for forming a SOLiD (Life Technologies, Carlsbad, Calif.) ordered array. The PEG additive slows the attachment of DNA coated bead to the surface and results in evenly spaced beads on the surface. In some embodiments, poly(ethylene glycol) having an average molecular weight of less than 350 Da was used, as shown in Example 2 below. Ethylene glycol, 2-methoxyethanol, 1,2-dimethoxyethanol poly(ethylene glycol), a methoxy or dimethoxy substituted PEG molecule, a discrete PEG such as diethylene glycol or tetra(ethylene glycol), a mixture thereof, or the like, can be used, as exemplified in FIG. 11.

According to various embodiments, the method enables the ability to deposit high densities of beads into grooves of an ordered array slide and to deposit high densities of beads with reduced bead sticking, clumping, and stacking. The method enables the ability to deposit higher densities of beads that are able to be individual mapped and reporter-detected, which increases instrument throughput per run. The method enables the ability to deposit beads side-by-side with a spacing gap between beads, which improves detection and isolation of each bead reporter. The method enables the ability to deposit beads side-by-side with a spacing gap between beads, which improves mapping of individual beads, and enables the ability to deposit beads side-by-side with a spacing gap between beads, which reduces noise contribution reported from adjacent beads. The method enables the ability to deposit beads with reduced bead stacking, enabling better image focusing. Moreover, the method enables the ability to deposit beads in an ordered array slide, and allows for improved algorithms to detect and analyze each individual bead signal reporter. Furthermore, the method enables the ability to deposit a higher concentration of beads on a surface efficiently and effectively, which reduces bead waste per deposition.

According to various embodiments, an ordered array of beads is provided that comprises a substrate comprising hydrophobic lines in the shape of a grid and at least one hydrophilic area defined between the hydrophobic lines. A monolayer of assay beads can be provided at each of the at least one hydrophilic areas. In some embodiments, the ordered array of beads comprises hydrophobic lines, a hydrophilic area, a combination thereof, or multiples thereof, that comprise a pattern of photo-resist, polydimethylsiloxane, metal, glass, metal oxide, or plastic.

According to yet other various embodiments of the present teachings, techniques for creating high capacity ordered arrays of beads are provided. To accommodate a higher number of samples, a gasket arrangement can be used that comprises polydimethylsiloxane (PDMS) or a similar material, to form separate confinement areas.

In some embodiments, hydrophobic separators are provided between hydrophilic sample confinement areas. For example, hydrophobic lines can be used to form a grid with hydrophilic areas between. The hydrophobic lines can have a larger grid with wider hydrophobic spaces to accommodate larger sample volumes, and the sample can cover several hydrophilic areas. Yet larger lines creating larger areas, for example, from mid-sized areas composed of multiple smaller areas, can be created.

According to various embodiments, photo-resist, PDMS, or other similar materials can be used in place of a surface treatment. Plasma treating over a mask can be used to change surface energy, and thus make different regions hydrophilic or hydrophobic. Stamping or nano-imprinting, and silk screening, are additional options. In yet other embodiments, electro-wetting or opto-electro-wetting is used to form the appropriate patterns. In some embodiments, a surface treatment is used to create hydrophobic and hydrophilic areas. Patterns of photo-resist, PDMS, metals, or other materials can also be made. The resulting surface can then be further modified, if desired, to change the surface energy. In some embodiments, the surface energy can be modified by direct photo-modification. The photo-modification can include photo-cleavage, photo-activation, a combination thereof, and the like. Patterning of light can be done using masks, DLP technology, LCD technology, a combination thereof, interference patterns, or the like. In some embodiments, devices, systems, and methods as described in the following U.S. Patents and Published Patent Applications can be used: U.S. Pat. No. 3,736,042; U.S. Pat. No. 4,705,705; U.S. Pat. No. 5,143,854; U.S. Pat. No. 5,202,227; U.S. Pat. No. 5,324,591; U.S. Pat. No. 5,776,748; U.S. Pat. No. 5,985,551; U.S. Pat. No. 6,548,263; U.S. Pat. No. 6,921,636; US Patent Application Publication No. 2006/0286548; U.S. Pat. No. 4,447,140; U.S. Pat. No. 6,967,074; and U.S. Pat. No. 5,510,270; each of which is incorporated herein in its entirety, by reference.

According to various embodiments, a clonal library confinement is provided. As an alternative to a bridge amplification technique used to create randomly placed and spaced clonal clusters as a result of placing the universal primers uniformly over the slide, a pattern of primers can be used such that a grid is created. Such a pattern can be made using many of the methods described herein and described in the references incorporated herein. The methods can include using physical masking techniques by placing metal patterns to which desirable attachment chemistry binds, or by placing metal patterns to which an undesired chemistry does not bind. In some embodiments, the attachment of linkers to the primers can comprise reactions of photo-cleavable linkers, or the linkers can be photo-activatable. In some embodiments, the primers can have photo-cleavable terminators.

In yet other embodiments of the present teachings, physical barriers are created, such as micro-wells, using different materials which are not suitable for an attachment chemistry of choice.

In some embodiments, single molecule sequencing is provided that uses light focusing devices, for example, light pipes or the like. Other methods can be used to create a grid of attachment sites for target nucleic acids.

To overcome a Poisson distribution that causes some areas to have several different target molecules, and many with none, some embodiments make use of a zero mode waveguide technique, where a bead is attached to the target. After attachment via covalent bonding hybridization, ligation, biotin-streptavidin, a combination thereof, or the like, the bead or similar object blocks any other bead from the area of interest. As a result, a high percentage of sites can be utilized. If desired, the bead can then be removed, or left in place, and can be selected so as not to interfere with subsequent chemistry. Such an embodiment can be used with relatively larger or smaller features, for example, wells. A bead or similar target attachment structure can enable the isolation of a single template molecule.

According to various embodiments, a bridge PCR system is provided embodying one or more of the bead manipulation embodiments described herein. In some embodiments, a bead is used to physically block additional molecules from interaction with the target. A low concentration of beads, probably below that optimal for a Poisson distribution, can be used in some embodiments, for example, to perform a PCR reaction and/or another cyclical or repeatable reactions. An initial PCR reaction can be made to use most of the primers available in a single area, preventing the possibility of amplification in the event that a second molecule happens to bind to a remaining unused primer. Thus, after several cycles, most of the available spaces can be filled with clonal populations. In some embodiments, more cycles are used than would otherwise be used to ensure sufficiently complete usage of primers.

According to various embodiments, an ordered array maximizes the throughput of a sequencing system, by maximizing the surface area utilization and minimizing the number of pixels needed per sequencing site.

According to various embodiments, a method of imaging a plurality of uniformly-sized beads in a bead array is provided. The method comprises arranging a plurality of uniformly-sized beads in a plurality of grooves of a grooved substrate, to form an array. The grooves can be spaced apart from one another by a pitch equal to about 110% or more of a diameter of the beads. In some embodiments, the beads have a diameter and the grooves of the grooved plate are spaced apart from one another at a pitch of from about 125% to about 300% the diameter. In some embodiments, the pitch is from about 140% to about 160% of the diameter.

In some embodiments, the beads can be configured to form a plurality of single-file rows of beads in the respective grooves. Adjacent beads in each row can be touching one another, and each bead can comprise a respective analyte fixed to a surface of the bead. The respective analyte of each bead can be different than the respective analyte of at least one other bead of the plurality. The method can further comprise exciting the plurality of beads in the array such that a portion of the beads become excited and emits increased radiation intensity relative to a portion of the other beads.

In some embodiments, the method can comprise imaging the array with an optics system configured to resolve adjacent grooves of the plurality of grooves but not necessarily of sufficient resolution to resolve adjacent excited beads within a same groove. The imaging can comprise forming an image array data set. The method can also comprise identifying the position of each bead in the array. In some embodiments, whether or not each bead is excited can be determined based on the array data set. In some embodiments, the positions of unresolvable adjacent excited beads within a same groove can be determined from identifying unresolved groups of quantized length.

According to various embodiments, the portion of the plurality of beads that becomes excited can comprise about 30% or less of the total number of beads. In some embodiments, the exciting can comprise exposing the array to at least four different excitation conditions, and the imaging can comprise generating a plurality of array data sets, with each array data set representing the array under a different respective one of the excitation conditions. In some embodiments, the analyte can be polynucleotides and the method can further comprise determining a sequence of each different analyte based on the plurality of array data sets.

According to various embodiments, a system is provided that comprises a substrate, a plurality of beads, an imaging system and a processor. The substrate can comprise a plurality of grooves formed in a surface thereof, and the grooves can be spaced apart from one another at a pitch. The plurality of beads can be loaded in the grooves and form an array. For each groove, a plurality of the beads can form a row of beads in the groove and adjacent beads in the row can touch one another. The beads can be uniformly-sized of a given diameter, and the pitch can be from about 125% to about 300% of the diameter. The imaging system can have a resolution sufficient to resolve adjacent rows but insufficient to resolve adjacent beads within a same row under excited conditions. The excited conditions can be such that increased radiation is emitted from the bead compared to radiation emitted from the same bead under non-excited conditions.

The imaging system can be configured to generate an array data set. In some embodiments, the processor can be configured to identify the position of each bead in the array based on the array data set. In some embodiments, the positions of unresolvable adjacent excited beads within a same groove are determined from identifying unresolved groups of quantized length. If the quantized length is, for example, four units, it can be determined that there are four excited beads in a row forming the quantized length. In some embodiments, the pitch is from about 140% to about 160% of the diameter. In some embodiments, the system further comprises an excitation source configured to direct an excitation beam toward the array under at least one set of excitation conditions. In some embodiments, the at least one set of excitation conditions comprises at least four different sets of excitation conditions, for example, corresponding to conditions to excite four different fluorescent dyes useful for sequencing a polynucleotide.

Figure 12:
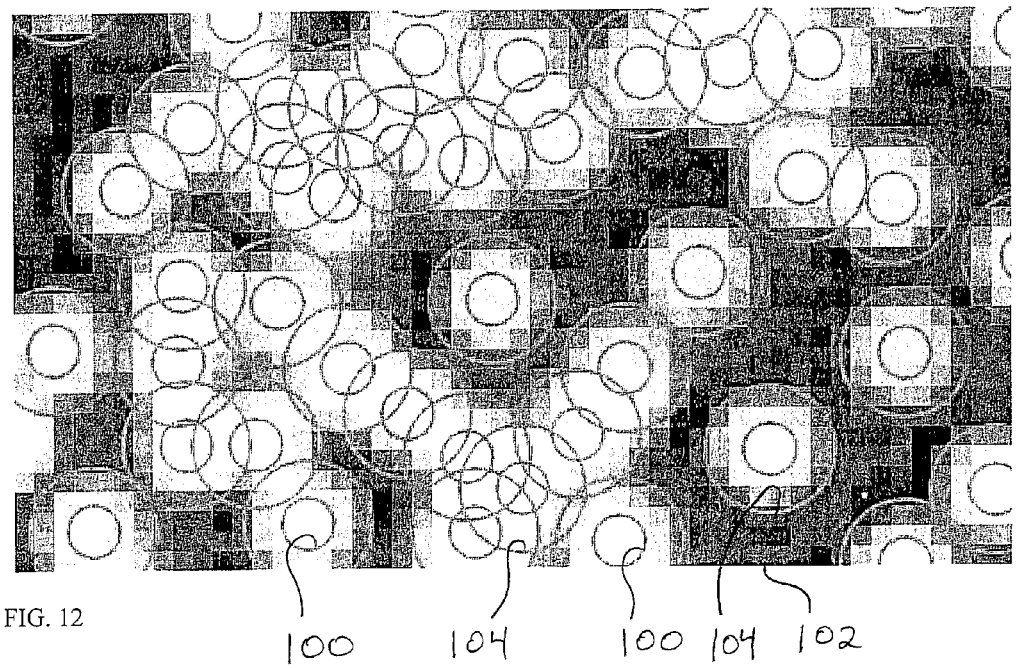
FIG. 12 shows beads randomly distributed on a slide and having no particular ordering.

In some embodiments, slides with V-grooves are used to order beads into an array whereby individual beads of the array can be identified a large packing densities can be used. For example, FIG. 12 shows beads at random distribution, less than full packing density, with unresolvable diffraction circles. According to various embodiments, a geometrically ordered separation is provided wherein a center-to-center separation of beads is present on the order of the diameter of the diffraction circle. Such an embodiment provides resolvable features at ordered coordinates that help recognition software identify bead locations. Ordering the beads in both 'x' and 'y' dimensions with a separation approximating the diffraction circle provides resolution in both dimensions.

Figure 16:
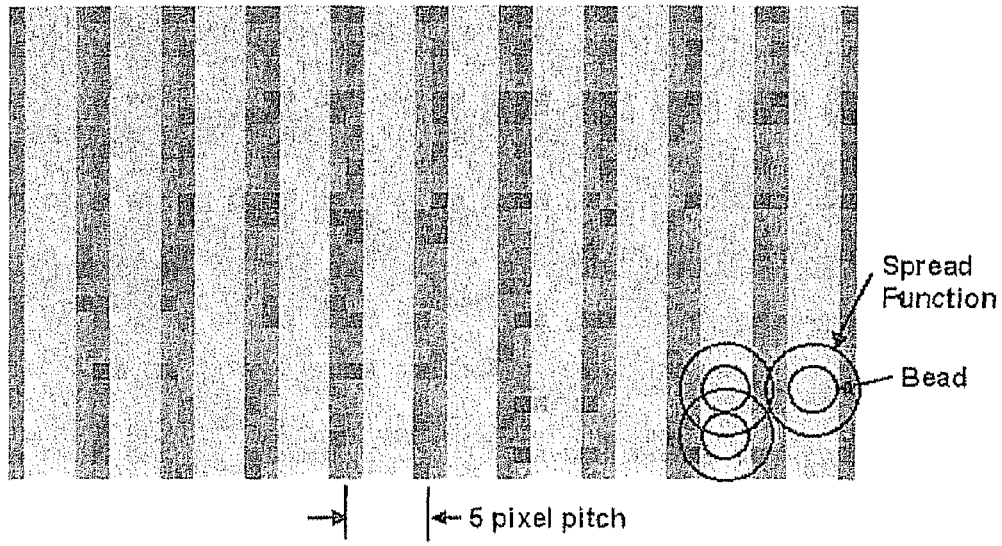
FIG. 16 is a simulated fluorescent image of the beads shown in FIGS. 14-15, showing all of the beads fluorescing, and demonstrates resolved rows of beads and unresolved beads within each of the rows.
Figure 17:
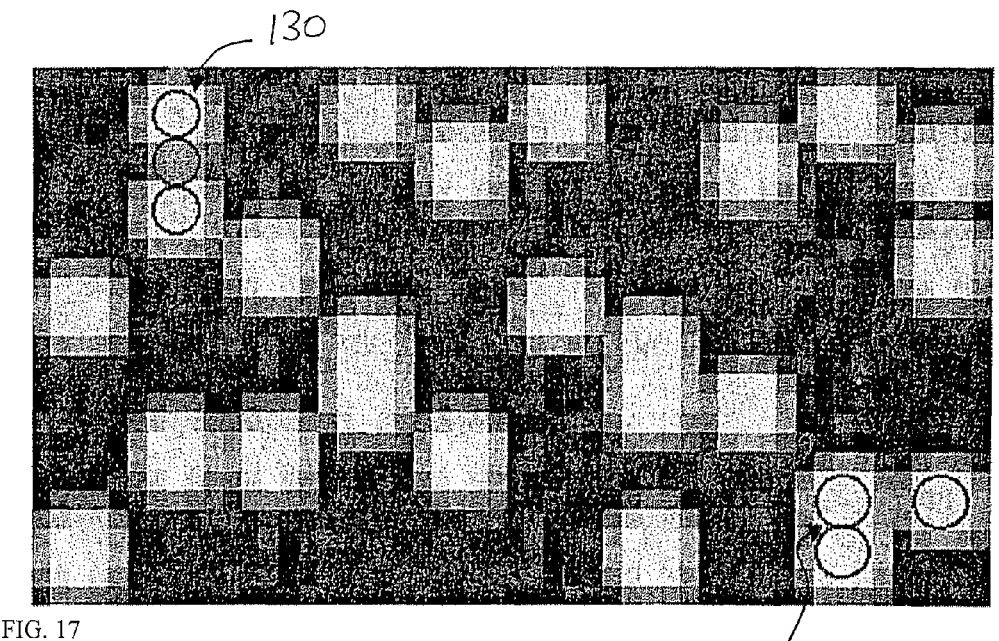
FIG. 17 is a simulated fluorescent image of the beads shown in FIGS. 14-15, showing a random 25% of the beads on the slide fluorescing, according to various embodiments of the present teachings.

In some embodiments, a packing density of about a factor of two can be achieved by ordering beads in each respective row. Beads that are not separated within the same row but instead touch each other can yield difficult to resolve diffraction circles as shown in FIG. 16. In some embodiments, however, such a packing scheme is used in a process where only a sub-population of the collection of beads lights up in any given image. In an example, beads used in a DNA sequencing method comprise a collection of beads with four different sub-populations, specifically, one for each of the nucleic acid bases A, C, G, and T. In some such applications, only one base can generate a signal in any given image. The beads which light up will appear as single beads, or as a group of a "quantized" length, depending on how many beads there are in a group of adjacent beads. An example of such a detection configuration is shown in FIG. 17, which makes clear gaps between groups. Such a configuration greatly simplifies a bead location software algorithm. In each successive base image, the beads will light up in a different grouping pattern, which data can be used to add further redundancy to the location specifics or addresses to be used with the algorithm.

According to some embodiments, beads are ordered in a row in a V-shaped groove, and the beads settle into the grooves. The rows can be separated at a 'pitch' on the order of the diffraction circle. In some embodiments, the rows can be separated at a 'pitch' on the order of about 110% or more of the average diameter of the beads, or from about 125% to about 300% the diameter, or from about 140% to about 160% of the diameter. The grooves can be created by etching, micromachining, nanoimprint lithography, and the like. In an exemplary embodiment, the beads are about 1 µm in diameter, and the rows are imaged at 20× magnification such that the imaged pitch of the rows on a CCD detector chip is equivalent to the length of five pixels.

According to various embodiments, photoactivatable attachment chemistry can be used to fix the beads to surfaces of each V-shaped channel. This and other chemistries can be used the enable jostling and/or settling of the beads into tight conformity, for example, in a touching, single-file order in the groove, before actual attachment or fixing to the groove surface.

Figure 13:
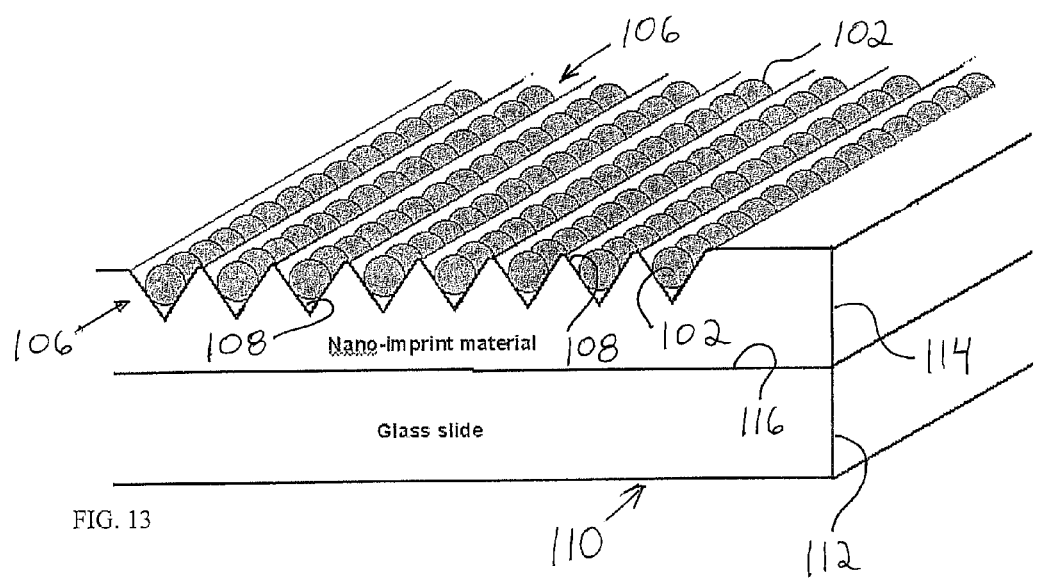
FIG. 13 shows an embodiment according to the present teachings wherein beads are arrayed in rows in V-grooves of a grooved plate.

FIG. 12 shows randomly distributed beads 100 on a slide 102, having no particular ordering. The bead density is well below a maximum density. FIG. 12 also shows a plurality of unresolvable diffraction circles 104. FIG. 13, on the other hand, shows an embodiment according to the present teachings wherein beads 102 are arrayed in rows 106 in V-grooves 108 of a grooved plate 110. As can be seen in FIG. 13, grooved plate 110 can comprise a glass slide 112 and a layer of nanoimprint material 114 on a top surface 116 of glass slide 112.

Figure 14:
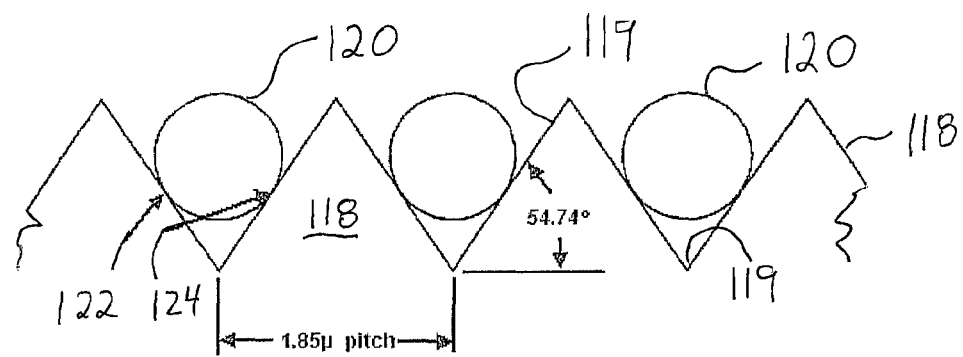
FIG. 14 is a side view of a slide showing exemplary dimensions that can be used for the groove angles and pitch in a configuration for ordering beads having a diameter of 1 µm, according to various embodiments of the present teachings.
Figure 15:
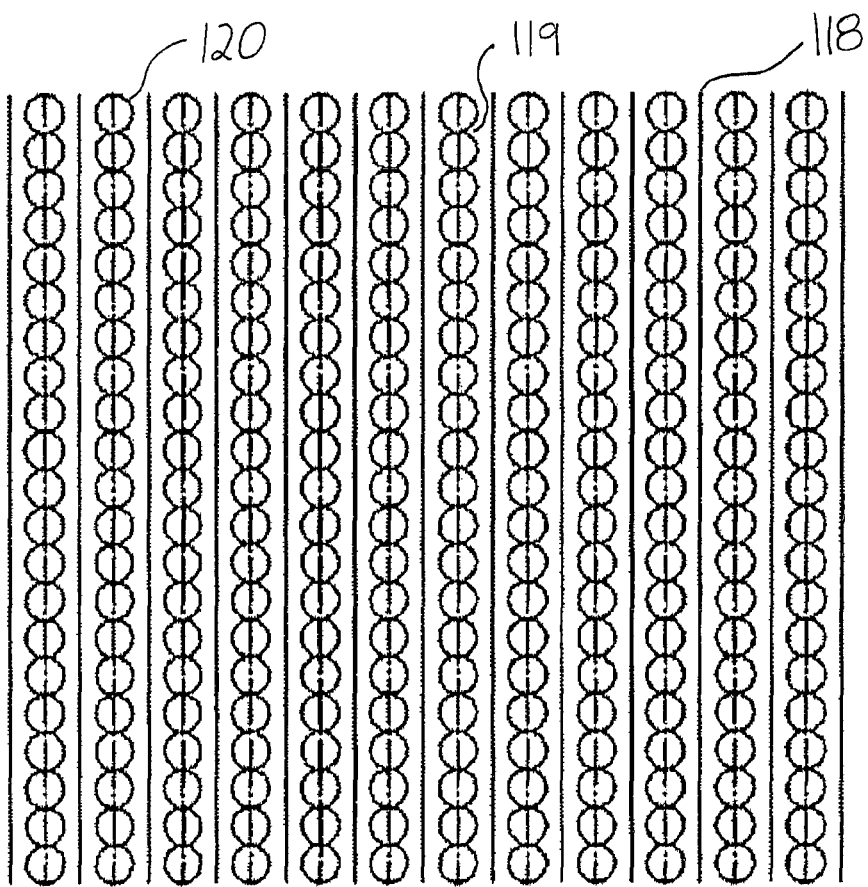
FIG. 15 shows a top plan view of the slide, grooves, and beads packed into rows, shown in FIG. 14.

FIG. 14 shows exemplary dimensions, according to various embodiments, that can be used for a slide 118 and grooves 119 configured to order beads 120 having a diameter of 1 µm. Although any groove shape, size, and angle can be used, the angle of about 54.74° and a V-shaped groove are exemplified because 54.74° is a silicon anisotropic etch angle. In the configuration shown in FIG. 14, each bead 120 contacts the surfaces of V-groove 119 at two contact points denoted 122 and 124. The 1.85 µm pitch is equivalent to the length imaged by five pixels of an exemplary CCD detector when the image is magnified 20 times. In some embodiments, the pitch can be equivalent to the length of from about 3 to about 20 pixels, from about 4 to about 10 pixels, or from about 5 to about 6 pixels of a pixilated detector when the pitch is magnified 20 times. FIG. 15 is a top plan view of the beads packed into rows shown in FIG. 14.

FIG. 16 shows a simulated fluorescent image of the beads shown in FIGS. 14-15, with all of the beads fluorescing, and demonstrates resolved rows and unresolved beads within rows. While the beads in each row are unresolved in FIG. 16, it is unlikely that all beads in a row would fluoresce at the same time in a DNA sequencing detection scheme. FIG. 17 shows a simulated fluorescent image of the beads shown in FIGS. 14-15, but with a random 25% of the beads fluorescing. As can be seen in FIG. 17, the beads appear either singly, or in unresolved groups of quantized length. According to various embodiments, even the unresolved groups of quantized length can be used to identify beads. In FIG. 17, it is readily discernable that two fluorescing beads can be identified with a single non-fluorescing bead in between them, as shown by bead group 130. Similarly, two adjacent beads that are both fluorescing can be identified at bead group 132.

By arranging beads as described herein, packing density can be maximized while resolution requirements are satisfied for beads having a large diffraction circle relative to the actual bead size. In the examples shown in FIGS. 14-15, beads can be ordered at two-fold the packing density of beads separated in both an 'X' and a 'Y' dimension, for example, at two-fold the density of beads disposed in a two-dimensional array of wells. In some embodiments, 1 micrometer (1 μm) diameter beads can be packed at a density of about 50 million beads per square centimeter ($cm^2$) such that at a 20× magnification, 300,000 beads can be imaged in a single 4 megapixel image. The location algorithms used for randomly packed beads break down at densities well below the densities that can be resolved according to the present teachings. The present method results in more robust bead location software algorithms and enables all of the beads on the slide to be readily addressable. The V-shaped groove or channel design increases the surface area of the slide in contact with the bead which captures beads more securely than beads attached to a planar surface, which can be more exposed to flow. Moreover, the configurations shown in FIGS. 13-15 provide two attachment points per bead rather than a single attachment point as is the case when attaching a bead to a planar surface.

According to various embodiments, the number of sequencable features per image is provided to achieve high throughput. Geometric ordering of the features results in higher feature density than random ordering, and in some embodiments hexagonal ordering is used to yield a maximum resolvable density. In some embodiments, the arrays comprise linearly ordered 1 micron beads arranged in troughs. In some embodiments, PEG can be used in the deposition buffer to retard the attachment process of the beads to the trough walls until the beads are fully settled and centered in the troughs. In some embodiments, PEG is used to impose a well defined bead separation of around 0.2 microns between the 1 micron beads. In some embodiments, such a spacing is used to facilitate bead identification and reduce bead-to-bead cross talk. In some embodiments, the loss in bead density relative to a perfect touching hexagonal packing, that results from keeping the beads slightly separated, is not a real loss in that without the separation many of the beads would not be identifiable or would suffer cross-talk with neighboring beads, rendering them unuseful.

According to various embodiments of the present teachings, a device is provided that comprises a substrate and a plurality of posts extending from a surface of the substrate. The plurality of posts can comprise a plurality of post clusters wherein one or more of the post clusters define bead receiving areas between posts. Each bead receiving area can be configured to retain a single bead of a predetermined bead diameter, for example, of a bead diameter of about 10 μm or less. In some embodiments, each post can comprise a base portion and a tip, and the cross-sectional area of the post can decrease in a direction from the base portion to the tip. In some embodiments, the post clusters are arranged to provide a center-to-center spacing of adjacent beads when disposed in the device, of from about 1.1 to about 1.9 times the diameter of a bead of the predetermined diameter. In some embodiments, the post clusters can be arranged to provide a center-to-center spacing of adjacent beads when disposed in the device, of from about 1.2 to about 1.6 times the diameter of a bead of the predetermined diameter. In some embodiments, the post clusters are arranged to provide a center-to-center spacing of adjacent beads, when disposed in the device, of about 1.5 times the diameter of a bead of the predetermined diameter. In some embodiments, the substrate can comprise an injection-molded polymer, for example, an injection molded cyclo-olefin polymer material.

In use, the device can comprise a plurality of beads, including one bead at each bead receiving area. In some embodiments, at least one fiducial post can be provided, disposed in at least one of the bead receiving areas. The at least one fiducial post can be configured to prevent a bead from being received in the respective bead receiving area. Each fiducial post can extend further from the surface than each post of the plurality of posts. In some embodiments, the device comprises a plurality of beads disposed in the bead receiving areas and forming an array, wherein the center-to-center spacing of the beads in the array is from about 115% to about 200% of the diameter of the beads.

According to various embodiments, a system is provided that comprises a device as described above, and an imaging system. The imaging system can have a resolution sufficient to resolve adjacent beads in the array, under excited conditions. The excited conditions can comprise, for example, conditions whereby increased radiation is emitted from the bead compared to radiation emitted from the same bead under non-excited conditions, and the imaging system being configured to generate an array data set. The system can further comprise a processor configured to identify the position of each bead in the array based on the array data set, and, for example, use a plurality of data sets to sequence an polynucleotide analyte.

Figure 18:
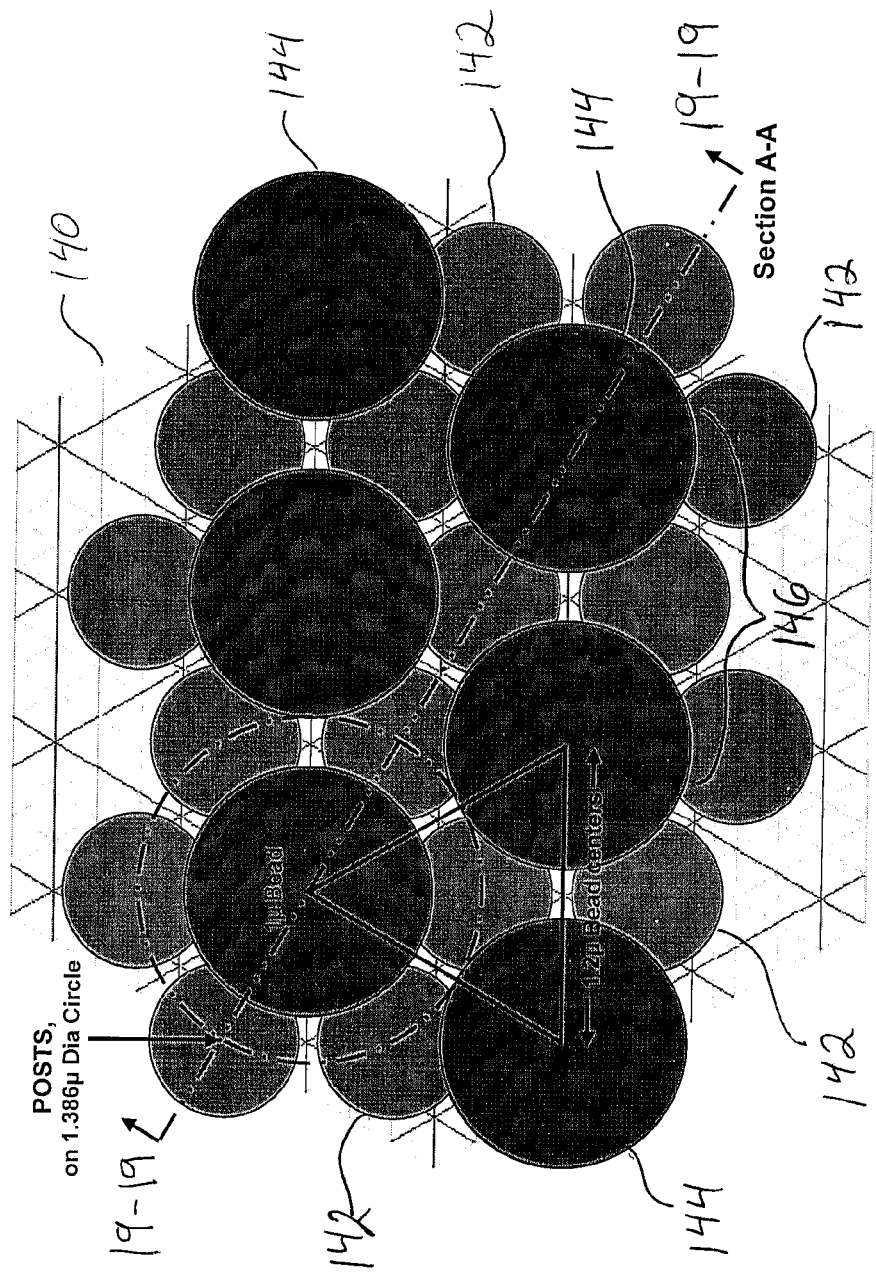
FIG. 18 is a top view of a slide and bead array according to various embodiments of the present teachings, wherein a slide is provided with strategically placed injection molded posts useful to locate beads having a diameter of one micrometer (1 µm) in a hexagonal array.
Figure 19:
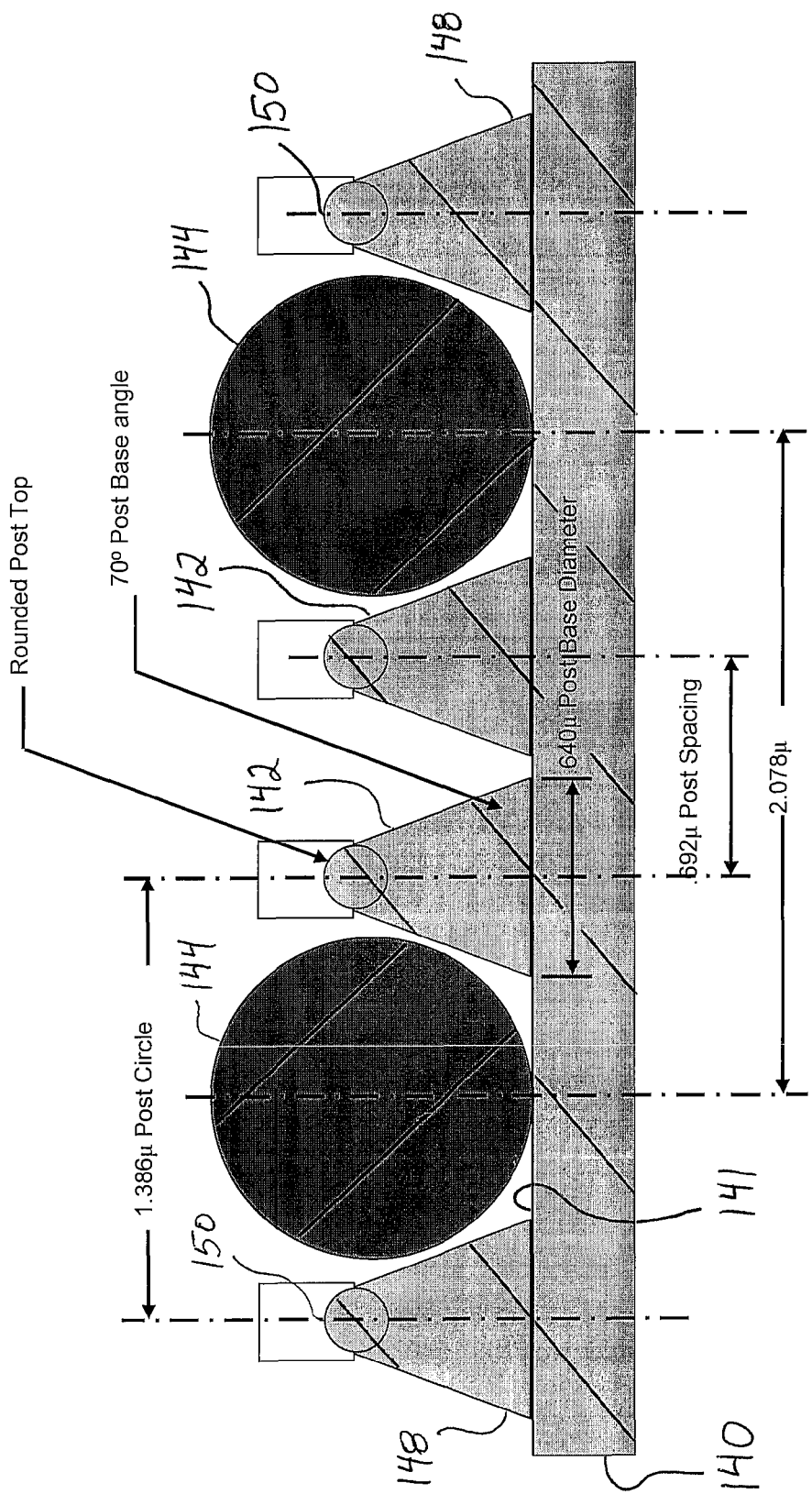
FIG. 19 is a cross-sectional side view taken along line 19-19 of FIG. 18.

In some embodiments, the maximum density of usable beads is achieved by a hexagonal array but wherein the beads are separated by just that amount of separation required to optimize bead identification and minimize bead-to-bead cross-talk. According to various embodiments, an injection molded polymer slide is used. Materials for such slides can be, for example, cyclo-olefin polymers. As exemplified in FIGS. 18 and 19, a slide 140 is provided with strategically placed injection molded posts 142 useful to locate beads 144 having a diameter of one micrometer (1 μm) in a hexagonal array 146. A separation distance between centers of 1.2 μm is provided between the centers of beads 144 by the locations of posts 142. Posts 142 can comprise a widened base portion 148 that narrows in cross-section as it comes to a tip 150 as shown in FIG. 19. FIG. 19 is a cross-sectional view taken along line 19-19 of FIG. 18. The tapered configuration of the posts facilitates ready entry of the beads into their desired locations, and locates the beads with a high degree of precision due to widened base portion 148. The dimensions shown are exemplary only, and not intended to limit the present teachings. As shown in FIG. 19, each post 142 has a rounded post top and intersects with a top surface 141 of slide 140 at an angle of 70° in the exemplary embodiment.

The formation of posts 142, while exemplified by injection molding, can be made by other methods, for example, by photoresist on a glass or polymer substrate, by micromachining, chemical etching, vapor deposition, and the like. In some embodiments, the maximum obtainable density of beads is obtained by ordering them into a hexagonal Array. Different post sizes, post shapes and, and post spacing can be used to control separation of beads of different diameters and/or to increase resolution under specific conditions. The posts can provide a separation that cannot be achieved, for example, by a self-assembled-monolayer (SAM), while at the same time the posts maintain density optimization of a hexagonal packing.

According to various embodiments, posts are used on a slide to provide optimal density packing of the beads on the slide and to provide entrapment of the beads. The entrapment can be sufficient to make them resistant to dislodgement by a fluid flow. Without entrapment or similar fixing of the beads, the result would be a loss of beads or wash-out of beads due to fluid flow over many cycles of flow.

According to various embodiments, a slide comprising a configuration of posts is provided wherein the arrangement of the posts permits a free fluid exchange between each bead and the surrounding fluid. The benefit is pronounced compared to devices wherein a bead is located in a fully surrounding well, particularly considering that the fit between the bead and the well would need to be fairly close in order to accurately locate the bead. Moreover, the benefit is pronounced in situations wherein reactions and viewing occur on the underside of the bead, at least because the underside of a bead in a fully surrounding well would experience impeded fluid exchange.

Figure 20:
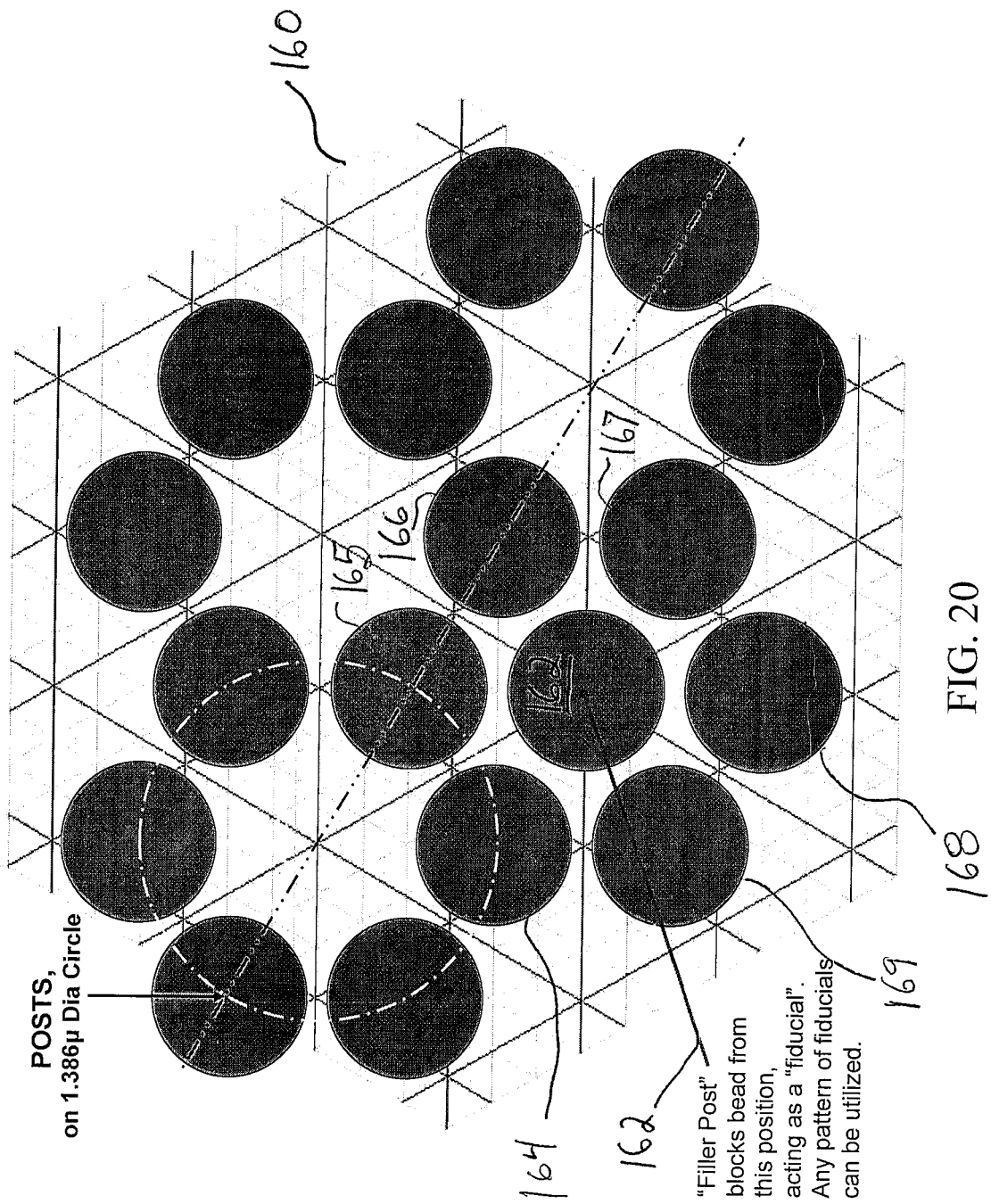
FIG. 20 is a top view of a slide comprising posts according to various embodiments of the present teachings, wherein the posts include a fiducial post.

FIG. 20 is a top view of a slide comprising posts according to various embodiments of the present teachings, wherein the posts include a fiducial post. As shown, a slide 160 is provided with an additional post 162 provided at the center of a post cluster formed by posts 164, 165, 166, 167, 168, and 169. In an example, additional post 162 can be, for example, larger than the surrounding posts and/or of a configuration that prevents a bead from being accepted or received at that location. Additional post 162 can exclude a bead from that position and/or act as a fiducial. In some embodiments, a pattern or array of additional posts 162, or filler posts, can be employed, for example, to code different image panels with different fiducial codings. In the embodiment, exemplary dimensions include posts having a base portion that intersects with a top surface of the slide at a circle having a diameter of 1.386 μm.

In some embodiments, the slides can be used with the Life Technologies (Carlsbad, Calif.) SOLiD platform.

According to various embodiments, a method of loading a plurality of magnetic beads into grooves of a grooved plate is provided. The method comprises first arranging a plate comprising grooves on a support such that grooves are vertically arranged. The support comprises an inclined surface and the grooves comprise respective first ends arranged adjacent the inclined surface, and respective open tops. A plurality of beads are then disposed, poured, or otherwise placed on the inclined surface such that gravitational, magnetic, centrifugal, or other forces can be used to cause the beads to traverse the inclined surface and enter the grooves at the first ends. The beads can be guided into the grooves in a manner such that beads in each groove are aligned with one another in each respective groove.

The guiding can comprise placing a guide wall adjacent the open tops in sufficiently close proximity to prevent the beads in any one of the grooves from moving into another one of the grooves. Subsequently, the beads can be fixed in the grooves. In some embodiments, the method further comprises separating the guide wall from adjacent the open tops and separating the plate from the support. The plate can comprise a first portion and a second portion, and the method can also comprise separating the first portion from the second portion after fixing the beads in the grooves, for example, also after separating the plate from the support. The beads can be fixed in the grooves by contacting the beads with a chemical fixing agent, magnetically attracting the beads against surfaces of the grooves, combinations thereof, or the like. In some embodiments, the beads can be guided into the grooves by magnetically attracting the beads into the grooves.

According to some embodiments, sequencing beads are placed in grooves of a grooved slide. The device and method can be used to increase packing density relative to a non-grooved slide by setting a small, uniform gap or pitch between rows of beads. The device enables beads to touch only adjacent beads along the dimension of the respective row defined by a groove of the slide. The device and method using same improve image resolution and interpretation. To minimize gaps between beads within the same row, a magnetic loading can be used according to various embodiments, as illustrated in FIGS. 21A-21C.

FIGS. 21A-21C depict a loading system and three successive steps of a loading method for magnetically loading and fixing beads into grooves of a slide. FIG. 21A shows a system 210 for loading a plurality of magnetic beads 212 into a slide 214 having a plurality of grooves 216. The system includes a support 211, and a slide 214. Support 211 comprises a first guide wall 218 and a second guide wall 220 that together are configured to guide beads 212 in a manner such that beads 212 slide into grooves 216 of slide 214. Support 211 can also comprise sidewalls 222 and 224 to help guide beads 212 into grooves 216. Beads 212 are magnetically forced into stacking inside grooves 216 by a magnet, and in the embodiment shown, a magnet 226 is provided to magnetically attract beads 212 into grooves 216. As magnet 226 pulls beads 212, guide walls 218 and 220 direct beads 212 into grooves 216. In some embodiments, the pitch of the grooves is from about 1.1 to about 2.5 times the bead diameter, for example, from about 1.3 to about 1.9 times, from about 1.4 to about 1.6 times, or about 1.5 times the bead diameter. For example, if beads having a diameter of 1.0 micrometer (μm) are to be used, the pitch of the grooves can be about 1.5 μm. After beads 212 are stacked in grooves 216, the resulting filled grooves are as shown in FIG. 21B.

In a next step of the method, and as shown in FIG. 21B, a second magnet 228 can be used to pull beads 212 against the bottom surface or surfaces of grooves 216. While a V-shaped cross-section groove is depicted, other groove shapes can be used, for example, a U-shaped groove or the like. In addition, or as an alternative, a fixing chemistry, depicted as droplet 230, can be used to chemically fix beads 212 in the grooves 216. While magnetic attraction and chemical treatments are exemplified as methods of fixing the beads in the grooves, other fixing methods can be used. Subsequent to fixing beads 212 in grooves 216, slide 214 bearing beads 212 can be separated from support 211 as an assembly 232.

FIG. 21C shows assembly 232 removed from support 211 and ready to load into an instrument, for example, into a DNA sequencing device. An exemplary platform that can be used with assembly 232 is the SOLiD sequencing platform available from Life Technologies, Carlsbad, Calif.

According to yet another embodiment of the present teachings, a method of loading a plurality of magnetic beads into grooves of a grooved plate is provided. The method can comprise use of a plate comprising a load portion, an excess portion, a plurality of grooves each having a respective open first end on the excess portion, a respective closed second end on the load portion, and a respective open top. The second ends can be closed by a sidewall and the sidewall can comprise an interior surface facing the grooves and an exterior surface facing away from the grooves. A magnet can be positioned or provided adjacent the exterior surface of the sidewall. Magnetic beads can then be loaded into the open ends of the grooves and can be magnetically attracted into the grooves, using the magnet.

In some embodiments, the beads in each groove can align with one another, for example, in a single file manner. After bead loading, the load portion of the plate can be separated from the excess portion of the plate. In some embodiments, the method can further comprise fixing the beads in the grooves, for example, with a chemical, with a magnet, with a combination thereof, or the like.

FIGS. 22A-22D depict four successive steps of a method and configuration for magnetically loading and fixing beads into grooves of a slide, and removing an excess slide portion, according to various embodiments of the present teachings. In FIG. 22A, a slide assembly 300 is provided into which a plurality of beads 302 are loaded. Beads 302 are forced into the slide, for example, by gravity or centrifugal force, and land randomly in grooves 304 formed in slide assembly 300. In some embodiments, the pitch of the grooves is from about 1.1 to about 1.9 times the bead diameter, for example, from about 1.3 to about 1.7 times, from about 1.4 to about 1.6 times, or about 1.5 times the bead diameter. For example, if beads having a diameter of 1.0 micrometer (μm) are to be used, the pitch of the grooves can be about 1.5 μm.

As seen in FIG. 22B, a magnet 306 located at a side and slightly below slide assembly 300, is used to attract beads 302 such that they stack up against a side wall 308 of slide assembly 300 and down into grooves 304.

FIG. 22C depicts a chemistry 310 being applied, and/or depicts the application of a new environmental condition, that fixes beads 302 into grooves 304. As shown in FIG. 22D, an excess portion 312 of slide assembly 300 is removed by cutting, breaking, ungluing, friction release, or the like, leaving a slide read assembly 314. Slide read assembly 314 is then ready to load into an instrument, for example, into a DNA sequencing device. An exemplary platform that can be used with assembly slide read assembly 314 is the SOLiD sequencing platform available from Life Technologies, Carlsbad, Calif. The throughput of such a device can be, for example, 60 GB for a run with 2 slides of 1 μm beads, using a 1.5 μm pitch between rows, considering a 68% slide fill factor, using DNA fragments of 35 base pairs (bp) on each bead.

Other devices, systems, and methods that can be used in conjunction with the present teachings include those described in US Patent Application Publications Nos. 2003/0165935 A1, published on Sep. 4, 2003, and 2005/0118589 A1, published on Jun. 2, 2005, both of which are incorporated herein in their entireties by reference.

The present teachings will be more fully understood with reference to the following Examples that are intended to illustrate, not limit, the present teachings.

EXAMPLES

Example 1

DNA-coated beads DH10 fragment library control SOLiD PN 4392462, Applied Biosystems, LLC, Foster City, Calif., are deposited at a loading density of 240,000 Control beads per panel area, on a zirconium coated ordered array slide. After pipetting the beads into a deposition chamber using standard SOLiD 3 deposition equipment and conditions, the slide, in the deposition chamber assembly, was centrifuged for 5 minutes at a force of 325×g=RCF, and the beads were bound within the groves of the ordered array slide.

FIG. 2 is a digital image of the resulting array, captured using a METAMORPH software package and Olympus microscope at 20× magnification. The image was digitally enhanced to 400% image after centrifugation. The dark clumps shown in the image of FIG. 2 are stacked beads.

A micro-abrasive bead wash solution was prepared by mixing together, in a 1.5 mL Eppendorf tube: 500 μL of 9.8% solid, 3.01 micron diameter Silica beads, from Bangs Laboratories, part number-SS05N/5411; and 100 μL of 10% solid, 4.74 micron diameter Silica beads, Bangs Laboratories, part number-SS05N/5568. The mixture was then centrifuged for two minutes in an Eppendorf centrifuge model 5415 at speed 14 (16,000×g=RCF). The liquid above the bead pellet was pipetted off and replaced with an equal amount of 100 mM NaCl. The mixture was vortexed and then centrifuged for two minutes in an Eppendorf centrifuge model 5415 at speed 14. The liquid above the bead pellet was pipetted off and raised to a final volume to 1000 μL of 100 mM NaCl.

The solution was then vortexed until the beads were completely resuspended. After the DNA-coated beads were deposited on the surface, the bead deposition buffer was removed from the chamber and enough abrasive bead solution was added to fill the volume of the chamber 60%. The partial filling left space in the chamber for the bead solution to flow within the chamber. The chamber with abrasive bead wash was placed onto a Roto-Torque rotation device with the rotation set to Low and the rotation speed was set to 7. The rotary was tilted approximately 60° and rotated for 15 minutes at room temperature. The rotation allowed the abrasive beads to roll over the deposited bead surface and to knock into the stacked beads. The disruption left a monolayer of beads on the surface. After 15 minutes, the abrasive bead solution was removed and the slide chamber was rinsed to remove wash solution beads and the disrupted DNA-coated beads.

The 240,000 bead deposition slide was then imaged again. FIG. 3 shows the result of the abrasive bead solution treatment showing most of the stacked beads removed. The treatment increased the number of individually detectable beads on the surface for sequencing.

Example 2

DNA-coated beads (DH10 fragment library control SOLiD PN 4392462-Applied Biosystems, LLC, Foster City, Calif.), with a loading of 260,000 Control beads per panel area, were deposited on a zirconium coated ordered array slide. The SOLiD DH10 Library control beads were prepared for deposition, on the SOLiD ordered array slides, by the following protocol resulting in the monolayer demonstrated in FIG. 6.

Step 1—In a first step, an aliquot of beads was dispensed into a 1.5 mL Eppendorf tube and placed into a magnet separator holder. After waiting a period of 2 minutes, the beads had collected on the side of the tube with the magnet and the solution was removed.

Step 2—A solution of 100 mM NaCl (100 μL) was added to the tube with the beads. After removing from the magnetic holder, the solution with beads was mixed by brief vortexing and then spun briefly at low RCF force with a table top centrifuge to pellet the liquid in the tube. The tube was then placed into the magnetic separator holder. After waiting a period of 2 minutes, the beads had collected on the side of the tube with the magnet and the solution was removed.

Step 3—Step 2 was repeated.

Step 4—A solution of 12% (V/V) PEG (200 MW) in 100 mM NaCl (100 μL) was added to the beads. The tube was then removed from the magnetic holder, mixed by brief vortexing and then spun briefly at low RCF force with a table top centrifuge to pellet the liquid in the tube. The tube was then placed into the magnetic separator holder, After waiting a period of 2 minutes, the beads had collected on the side of the tube with the magnet and the solution was removed.

Step 5—More of the solution of 12% (V/V) PEG (200 MW) in 100 mM NaCl (500 μL) was added to the tube with beads. The tube was then removed from the magnetic holder, mixed by brief vortexing and then spun briefly at low RCF force with a table top centrifuge to pellet the liquid in the tube.

Step 6—The tube containing the PEG mixture with the beads was then placed into a Covaris sonicator and sonicated using the Enrich 01 protocol. After Covaris treatment, the tube was removed from the device and spun briefly at low RCF force with a table top centrifuge to pellet the liquid in the tube.

Step 7—The solution of DNA coated beads in the PEG containing solution was then pipetted into a full slide SOLiD deposition chamber containing a zirconium coated ordered array slide. The chamber was tilted slightly to allow the liquid to flow up in one continuous slow, even, bubble-free front. After the chamber was full, sticky tabs were used to completely seal the chamber holes.

Step 8—The deposition chamber was placed into Beckman Allegra Centrifuge, with a swinging bucket rotor, and spun at 162-197 RCF for 5 minutes. FIGS. 6 and 8 show the beads on the slide following deposition.

In Example 2, the Polyethylene Glycol that was used had an average MW of 200 DA, available as part number P3015 from Sigma Aldrich Chemical. The NaCl that was used is available from Sigma as part number S-3014. The 100 mM NaCl solution was prepared in deionized sterile water.

The Covaris Enrich01 protocol used was as follows:

```
Number of Cycles = 4
Bath Temperature Limit (C.) = 20.000000
Mode = "Frequency Sweeping"
Water Quality Testing = FALSE
[Treatments]

Number of Treatments = 4
[Treatment 0]

Cycles per Burst = 1
Time(sec) = 5.000000
Duty Cycle (%) = 2.000000
Intensity = 6.000000
[Treatment 1]

Cycles per Burst = 1
Time(sec) = 30.000000
Duty Cycle (%) = 5.000000
Intensity = 9.000000
[Treatment 2]

Cycles per Burst = 0
Time(sec) = 0.000000
Duty Cycle (%) = 0.100000
Intensity = 0.100000
[Treatment 3]

Cycles per Burst = 0
Time(sec) = 0.000000
Duty Cycle (%) = 0.100000
Intensity = 0.100000
```

One skilled in the art will appreciate further features and advantages of the present disclosure based on the above-described embodiments. Accordingly, the present disclosure is not to be limited by what has been particularly shown and described, except as indicated by the appended claims. All publications and references cited herein are expressly incorporated herein by reference in their entirety.

The invention claimed is:

1. A method comprising:
   washing an array of first beads on a substrate, a surface of which contains a plurality of channels, microwells, or posts, with a wash solution to remove stacked first beads from the substrate, the wash solution comprising from 2% to 50% by weight inert solid beads, the first beads having an average diameter and the solid beads having an average diameter that is at least twice the average diameter of the first beads, the washing dislodging the stacked first beads; and
   removing the wash solution and the dislodged first beads from the substrate to form a monolayer of first beads disposed in said channels or microwells or between said posts, forming an array, wherein for a channel of said channels, a plurality of the first beads forms a row of first beads in said channel, the row being substantially free of stacked first beads, or wherein for each microwell of a plurality of said microwells or between each set of posts of a plurality of said posts, an individual first bead is disposed substantially free of a stacked first bead.

2. The method of claim 1, wherein the substrate comprises a slide.

3. The method of claim 1, wherein the channels are formed in a surface thereof.

4. The method of claim 1, wherein the first beads comprise DNA-coated beads.

5. The method of claim 1, wherein the carrier comprises water.

6. The method of claim 1, wherein the inert solid beads of the wash solution comprise first solid beads having a second average diameter, and second solid beads having a third average diameter, and the second average diameter is at least 50% greater than the third average diameter.

7. The method of claim 1, further comprising:
   contacting a plurality of the first beads with a poly(ethylene glycol) (PEG) solution comprising a PEG having a molecular weight of about 350 Da or less, to form a bead mixture; and
   depositing the bead mixture on the surface of the substrate.

8. The method of claim 7, wherein the PEG has a molecular weight of 100 DA to 300 Da.

9. The method of claim 8, wherein the molecular weight is 150 Da to 250 Da.

10. The method of claim 7, wherein depositing comprises depositing the bead mixture into the channels or the microwells or between the posts.

11. The method of claim 10, wherein the channels have a pitch of 125% to 300% of the diameter of the first beads.

12. The method of claim 1, wherein the inert solid beads have a density from 1.0 g/cc to 3.0 g/cc.

13. The method of claim 1, wherein the average diameter of the inert solid beads is in a range of 3 to 5 micrometers.

14. The method of claim 1, wherein the inert solid beads comprise silica, silicon nitride, or boron nitride.

15. A method comprising:
    depositing a plurality of nucleic acid-coated beads on a substrate to form an array of nucleic acid-coated beads, a subset of the plurality of nucleic acid-coated beads forming stacked beads;

washing the substrate with a wash solution to dislodge a plurality of the stacked beads from the substrate, the wash solution comprising from 2% to 50% by weight inert solid beads, the nucleic acid-coated beads having an average diameter and the solid beads having an average diameter at least twice the average diameter of the nucleic acid-coated beads; and removing the wash solution and the dislodged stacked beads from the substrate.

16. The method of claim 15, wherein the nucleic acid-coated beads include DNA-coated beads.

17. The method of claim 15, wherein the substrate comprises a slide having a plurality of grooves in a surface thereof, and the depositing comprises depositing the plurality of nucleic acid-coated beads into the grooves.

18. The method of claim 15, wherein the inert solid beads of the wash solution comprise first solid beads having a second average diameter, and second solid beads having a third average diameter, and the second average diameter is at least 50% greater than the third average diameter.

19. The method of claim 15, wherein the inert solid beads have a density from 1.0 g/cc to 3.0 g/cc.

20. The method of claim 15, wherein the average diameter of the inert solid beads is in a range of 3 to 5 micrometers.

* * * * *